United States Patent [19]

Fischli et al.

[11] Patent Number: 4,929,741
[45] Date of Patent: May 29, 1990

[54] PROPIOLOPHENONE DERIVATIVES

[75] Inventors: Albert Fischli, Riehen, Switzerland; Eva-Maria Gutknecht, Buggingen-Seefelden, Fed. Rep. of Germany; Daniel Obrecht, Basel, Switzerland

[73] Assignee: Hoffman-La Roche Inc., Nutley, N.J.

[21] Appl. No.: 169,643

[22] Filed: Mar. 17, 1988

[30] Foreign Application Priority Data

Mar. 20, 1987 [CH] Switzerland ............... 1072/87

[51] Int. Cl.$^5$ ............................. C07D 317/44
[52] U.S. Cl. ........................ 549/447; 549/441; 549/444; 549/446; 568/331; 568/335; 568/336; 568/337; 568/42; 568/43; 564/446; 564/442; 564/443; 564/169; 560/254; 560/50; 560/53; 562/459; 562/463
[58] Field of Search ............. 562/459, 449, 463; 549/447, 441, 444, 446; 568/331, 335, 336, 337, 42, 43; 564/446, 442, 443, 169; 560/254, 50, 53

[56] References Cited

U.S. PATENT DOCUMENTS

| | | | |
|---|---|---|---|
| 3,705,177 | 12/1977 | Subroya et al. | 568/336 |
| 3,754,021 | 8/1973 | Shen et al. | 562/459 |
| 4,333,952 | 6/1982 | McDonald | 568/336 |
| 4,450,292 | 5/1984 | Christidis et al. | 562/463 |
| 4,483,868 | 11/1984 | Christidis et al. | 562/459 |
| 4,500,731 | 2/1985 | Bianchi et al. | 562/463 |
| 4,594,443 | 6/1986 | Bianchi et al. | 562/463 |
| 4,708,966 | 11/1987 | Loomans et al. | 568/337 |

FOREIGN PATENT DOCUMENTS

| | | | |
|---|---|---|---|
| 0157740 | 10/1985 | European Pat. Off. | 568/331 |
| 2075836 | 11/1981 | United Kingdom | 562/463 |

*Primary Examiner*—James H. Reamer
*Attorney, Agent, or Firm*—George M. Gould; Bernard S. Leon; Alan P. Kass

[57] ABSTRACT

Propiolophenone derivatives of the formula

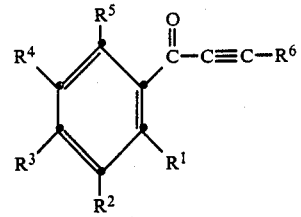

I wherein $R^6$ is hydrogen, lower alkyl or a group of the formula

| | |
|---|---|
| $-COOR^7$, | (a) |
| $-CONR^8R^9$, | (b) |
| $-C(R^{10})=O$, | (c) |
| $-C(R^{11})(OR^{12})_2$, | (d) |
| $-C(OR^{13})_3$ | (e) | or

| | |
|---|---|
| $-C(R^{14})(R^{15})OR^{16}$; | (f) | as well as corresponding hydroxy compounds of the formula

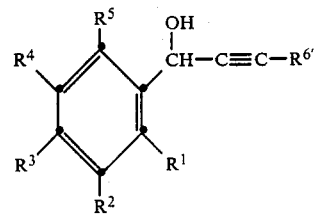

II wherein $R^{6'}$ is hydrogen, lower alkyl, a group of formula (a), (b), (c), (d) or (e) or a group of the formula

| | |
|---|---|
| $-C(R^{14})(R^{15})OR^{16'}$ | (f'): | exhibit mucosa-protective and/or gastric acid secretion-inhibiting properties, such that they can be used for the control or prevention of illnesses of the gastrointestinal tract, especially against gastric ulcers and/or duodenal ulcers.

25 Claims, No Drawings

PROPIOLOPHENONE DERIVATIVES

BACKGROUND OF THE INVENTION

The present invention relates to propiolophenone derivatives. In particular, it is concerned with propiolophenone derivatives of the formula

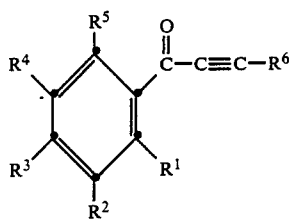

wherein $R^1$, $R^2$, $R^3$, $R^4$ and $R^5$ are independently hydrogen, halogen, lower alkyl, lower alkoxy-lower-alkyl, hydroxy, lower alkoxy, lower alkenyloxy, lower alkynyloxy, lower alkoxy-lower alkoxy, acyloxy, aryl-lower-alkoxy, lower alkylthio, lower alkoxy-lower-alkylthio, lower alkenylthio, lower alkynylthio, aryl lower-alkylthio, optionally substituted amino or trifluoromethyl, or two of these substituents which are adjacent jointly and together with the carbon atoms to which they are attached form a 5- to 7-membered ring, provided that of the substituents $R^1$ to $R^5$ at least two are hydrogen and at least one is different from hydrogen; and R6 is hydrogen, lower alkyl or a residue of the formula —COOR$^7$, (a)

—CONR$^8$R$^9$, (b)

—C(R$^{10}$)=O, (c)

—C(R$^{11}$)(OR$^{12}$)$_2$, (d)

—C(OR$^{13}$)$_3$ (e)

or

—C(R$^{14}$)(R$^{15}$)OR$^{16}$; (f)

$R^7$ is hydrogen, lower alkyl, lower alkenyl, lower alkoxy-lower-alkyl, lower alkoxy-lower-alkoxy-lower-alkyl, aryl or aryl-lower-alkyl; $R^8$ and $R^9$ are independently hydrogen or lower alkyl, or jointly and together with the nitrogen atom form a 5- to 7-membered saturated heterocyclic group; $R^{10}$ is hydrogen, lower alkyl, aryl or aryl-lower-alkyl; $R^{11}$ is hydrogen, lower alkyl, aryl or aryl-lower-alkyl; $R^{12}$ is lower alkyl or lower alkoxy-lower-alkyl; $R^{13}$ is lower alkyl; $R^{14}$ and $R^{15}$ are independently hydrogen, lower alkyl, aryl or aryl-lower-alkyl; and $R^{16}$ is hydrogen, lower alkyl, lower alkoxy- lower-alkyl, lower alkenyl, lower alkynyl, acyl or aryl-lower-alkyl; as well as pharmaceutically acceptable salts of acidic compounds of formula I with bases and of basic compounds of formula I with acids.

These compounds are novel with the exception of:
4-methoxy-1-(3-methylphenyl) 2-butyn-1-one;
4-methoxy-1-(4-methoxyphenyl)-4-methyl-2-pentyn-1-one;
4-methoxy-4 methyl-1-(3-methylphenyl)-2 pentyn-1-one;
methyl 3-(2,6-dimethoxybenzoyl)propiolate and
N,N diisopropyl-3-(2-hydroxy-5-methylbenzoyl) propiolamide, and it has been found that they possess valuable pharmacodynamic properties, namely mucosa-protective and/or gastric acid secretion-inhibiting properties, such that they can be used for the control or prevention of illnesses of the gastrointestinal tract, especially against gastric ulcers and/or duodenal ulcers.

Aspects of the present invention comprise the compounds and salts defined earlier as therapeutically active substances, medicaments containing such a compound or a salt thereof, and the use of the compounds and salts defined earlier in the control or prevention of illnesses, especially in the control or prevention of gastric ulcers and/or duodenal ulcers.

The term "lower" denotes compounds or residues with a maximum of 7, preferably a maximum of 4, carbon atoms.

The term "alkyl" denotes straight-chain or branched saturated hydrocarbon residues such as methyl, ethyl, n-butyl and the like. The terms "alkoxy" and "alkylthio" denote alkyl groups in the sense of the previous definition attached via an oxygen atom and a sulphur atom, respectively, such as methoxy and methylthio, respectively, and the like. The terms "alkenyl" and "alkynyl" denote hydrocarbon groups which contain a carbon-carbon double or triple bond, for example, groups such as dimethylallyl. The term "aryl" denotes an optionally substituted phenyl group such as 4-methoxyphenyl, 3,4-methylenedioxyphenyl,2,4,6-trimethylphenyl, 3,4,5-trimethoxyphenyl and the like. The term "acyl" embraces lower alkanoyl groups such as acetyl or the like and aroyl groups (i.e., arylcarbonyl groups) such as 3,4,5-trimethoxybenzoyl and the like. The term "halogen" embraces the four forms: chlorine, fluorine, bromine and iodine. The term "optionally substituted amino" denotes an amino group which can be monosubstituted by lower alkyl or acyl or disubstituted by lower alkyl and acyl or by two lower alkyl residues.

The 5- to 7-membered ring which two adjacent substituents $R^1$, $R^2$, $R^3$, $R^4$, $R^5$ together With the carbon atoms to which they are attached can form can be heterocyclic or carbocyclic. This ring can optionally contain one or more additional double bonds, in which case it can be aromatic or non-aromatic, and the ring can be substituted or unsubstituted. The 5- to 7-membered saturated heterocyclic residue which $R^8$ and $R^9$ together with the nitrogen atom can form can contain an additional hetero atom and it can be substituted or unsubstituted.

For example, $R^1$, $R^2$, $R^3$, $R^4$ and $R^5$ can independently be hydrogen, halogen, lower alkyl, hydroxy, lower alkoxy, lower alkylthio or di-lower alkylamino or two of these substituents which are adjacent can together be lower alkylene or lower alkylenedioxy, provided that of the substituents $R^1$ to $R^5$ at least one is different from hydrogen and at least two are hydrogen, preferably $R^1$ is hydrogen.

Preferably, in formula I $R^1$ and $R^2$ are hydrogen and $R^3$, $R^4$ and $R^5$ are lower alkoxy; or $R^1$ and $R^5$ are hydrogen and $R^2$, $R^3$ and $R^4$ are lower alkoxy; or $R^1$, $R^3$ and $R^4$ are hydrogen and $R^2$ and $R^5$ are lower alkoxy; or $R^1$, $R^2$ and $R^5$ are hydrogen and $R^3$ and $R^4$ together are lower alkylenedioxy or lower alkylene; or $R^1$, $R^2$, $R^4$ and $R^5$ are hydrogen and $R^3$ is halogen, lower alkyl, hydroxy, lower alkoxy, lower alkylthio or di-lower alkylamino; $R^6$ is a residue of formula (a), (b), (c), (d), (e) or (f) in which $R^7$ is hydrogen, lower alkyl, lower alkoxy-lower-alkoxy-lower alkyl, aryl-lower alkyl or lower alkenyl, $R^8$ and $R^9$ are lower alkyl, is hydrogen, $R^{11}$ is hydrogen, $R^{12}$ is lower alkyl, $R^{13}$ is lower alkyl, $R^{14}$ is hydrogen, $R^{15}$ is hydrogen or lower alkyl and $R^{16}$ is hydrogen, lower alkenyl, lower alkoxy-lower-alkyl or acyl.

Among the compounds of formula I there are especially preferred those in which $R^1$ and $R^2$ are hydrogen and $R^3$, $R^4$ and $R^5$ are methoxy, or $R^1$ and $R^5$ are hydrogen and $R^2$, $R^3$ and $R^4$ are methoxy, or $R^1$, $R^3$ and $R^4$ are hydrogen and $R^2$ and $R^5$ are methoxy, or $R^1$, $R^2$ and $R^5$ are hydrogen and $R^3$ and $R^4$ together are methylenedioxy, or $R^1$, $R^2$, $R^4$ and $R^5$ are hydrogen and $R^3$ is chlorine, fluorine, methyl, hydroxy, methoxy or methylthio, and in which $R^6$ is a residue of formula (a), (b) or (f) in which $R^7$ is hydrogen, methyl or methoxyethoxyethyl, $R^8$ and $R^9$ each is methyl, $R^{14}$ is hydrogen, $R^{15}$ is hydrogen or methyl and $R^{16}$ is hydrogen or 1-ethoxyethyl.

3-[3,4-(Methylenedioxy)benzoyl]propiolic acid is a particularly preferred compound of formula I.

Additional especially preferred compounds of formula I are:

4-hydroxy 1-(3,4,5-trimethoxyphenyl)-2-butyn-1-one;
3-(4-methoxybenzoyl)propiolic acid;
methyl 3-(2,3,4-trimethoxybenzoyl)propiolate;
methyl 3-(4-hydroxybenzoyl)propiolate;
2-(2-methoxyethoxy)ethyl 3-(3,4 5-trimethoxybenzoyl)-propiolate;
2-(2-methoxyethoxy)ethyl 3-(4-methoxybenzoyl)-propiolate;
methyl 3-(2,5-dimethoxybenzoyl)propiolate;
3-(2,5-dimethoxybenzoyl)propiolic acid; and
2-(2-methoxyethoxy)ethyl 3-[3,4-(methylenedioxy)-benzoyl]propiolate.

Further preferred compounds of formula I are:

3-(2,3,4-trimethoxybenzoyl)propiolic acid;
3-(3,4,5-trimethoxybenzoyl)propiolic acid;
methyl 3-(4-fluorobenzoyl)propiolate;
methyl 3-(3,4,5-trimethoxybenzoyl)propiolate;
N,N-dimethyl-3-(3,4,5-trimethoxybenzoyl)propiolamide;
1-(4-fluorophenyl)-4-hydroxy-2-butyn-1-one;
4-hydroxy-1-(4-methylphenyl)-2-butyn-1-one;
4-(1-ethoxyethoxy)-1-(4-fluorophenyl)-2-butyn-1 one;
1-(4-chlorophenyl)-4-hydroxy-2-butyn-1-one;
4-hydroxy-1-(4-methoxyphenyl)-2-butyn-1-one
4-hydroxy-1- 3,4 methylenedioxy)phenyl]-2-butyn-1.one;
4-hydroxy-1-(3,4,5-trimethoxyphenyl)-2-pentyn-1-one;
4-(1-ethoxyethoxy)-1-(2,3,4-trimethoxyphenyl)-2 butyn.1one;
4-hydroxy-1-(2,3,4-trimethoxyphenyl)-2-butyn-1-one; and
4-hydroxy-I-[4-(methylthio)phenyl]-2 butyn 1-one.

The novel propiolophenone derivatives of formula I defined earlier and their salts can be prepared by the following procedures:

(a) oxidizing a compound of the formula

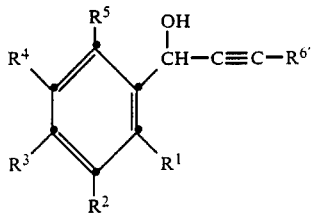

wherein $R^1$, $R^2$, $R^3$, $R^4$ and $R^5$ have the above mentioned meanings and $R^{6'}$ is hydrogen lower alkyl, a group of formula (a), (b), (c), (d) or (e) or a group of the formula $$-C(R^{14})(R^{15})OR^{16'} \qquad (f')$$

in which $R^{14}$ and $R^{15}$ have the above mentioned meanings and $R^{16'}$ is as defined above for $R^{16}$ but hydrogen when $R^{14}$ and/or $R^{15}$ are hydrogen;, or (b) cleaving off the protecting group(s) from a compound of the formula

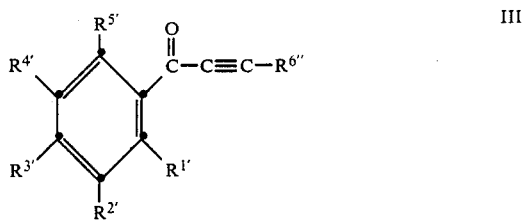

wherein $R^{1'}$, $R^{2'}$, $R^{3'}$, $R^{4'}$ and $R^{5'}$ have the meanings given above for $R^1$, $R^2$, $R^3$, $R^4$ and $R^5$ and a maximum of three of them can additionally represent protected hydroxy, protected amino or protected lower alkylamino, $R^{6''}$ is a residue of formula (a), (b), (c), (d), (e) or $$-C(R^{14})(R^{15})OR^{16''} \qquad (f'')$$

in which $R^{14}$ and $R^{15}$ have the above meanings and $R^{16''}$ has the same meaning given above for $R^{16}$ and can additionally represent a protecting group, whereby the molecule contains at least one protecting group; or (c) reacting a compound of the formula

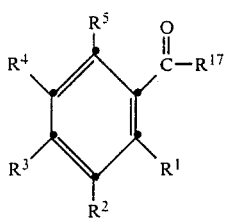

Wherein $R^1$, $R^2$, $R^3$, $R^4$ and $R^5$ are as defined above and $R^{17}$ is a leaving group, with a compound of the formula $$HC\equiv C-R^{6'''} \qquad V$$

wherein $R^{6'''}$ is a group of formula (a), (b), (d), (e) or (f);

(d) cleaving a compound of formula I in which $R^6$ is a group of formula (a) wherein R is different from hydrogen, to the corresponding carboxylic acid, or (e) acylating a compound of formula I in which $R^6$ is a group of formula (f) in which $R^{16}$ is hydrogen; or (f) converting a compound of formula I in which $R^6$ is a group of formula (d) into the corresponding compound of formula I in which $R^6$ is a group of formula (c); or (g) converting an acidic compound of formula I with a base or a basic compound of formula I with an acid into a pharmaceutically acceptable salt.

The compounds of formula II have similar pharmacodynamic properties to the propiolophenone derivatives of formula 1, primarily those in which $R^{6'}$ is a group of formula (a) above in which $R^7$ is especially lower alkyl or lower alkoxy-lower-alkoxy-lower-alkyl. Representative examples of such compounds are: methyl 4-hydroxy-4-[3,4-(methylenedioxy)-phenyl]-2-butynoate and 2-(2-methoxyethoxy)ethyl-4-hydroxy-4-(3,4,5-trimethoxyphenyl)-2-butynoate. The compounds of formula II are novel with the exception of ethyl 4-(2,5-dimethoxyphenyl)-4-hydroxy-2-butynoate;
ethyl 4-(2-methoxyphenyl)-4-hydroxy-2-butynoate;
methyl 4-(2-benzyloxy-6-methoxyphenyl)-4-hydroxy-2 butynoate;
4-(2-benzyloxy-6-methoxyphenyl) 4 hydroxy-2-butynoic acid; and
4-(2,6-dimethoxyphenyl)-4-hydroxy-2-butynoic acid.

A further aspect of the present invention is. accordingly, compounds of formula II which are useful as therapeutically active substances, pharmaceutical compositions containing such a compound, and the use of such compounds of formula II in the control or prevention of illnesses, especially in the control or prevention of gastric ulcers and/or duodenal ulcers.

Preferably, in formula II $R^1$ and $R^2$ each are hydrogen and $R^3$, $R^4$ and $R^5$ each are lower alkoxy, or $R^1$ and $R^5$ each are hydrogen and $R^2$, $R^3$ and $R^4$ each are lower alkoxy, or $R^1$, $R^2$ and $R^5$ each are hydrogen and $R^3$ and $R^4$ together are lower alkylenedioxy or lower alkylene, or $R^1$, $R^2$, $R^4$ and $R^5$ each are hydrogen and $R^3$ is halogen, lower alkyl, hydroxy, lower alkoxy, lower alkylthio or di-lower alkylamino.

The novel compounds of formula II can be prepared by the following procedures:

(aa) reacting a compound of the formula

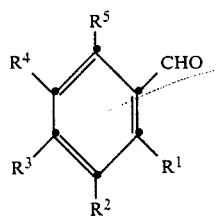

VI wherein $R^1$, $R^2$, $R^3$, $R^4$ and $R^5$ are as defined above, with a compound of the formula $$HC\equiv C-R^{6iv} \quad\quad Va$$

wherein $R^{6iv}$ is a group of formula (a), (b), (d), (e) or (f); or (bb) cleaving off the protecting group(s) from a compound of the formula

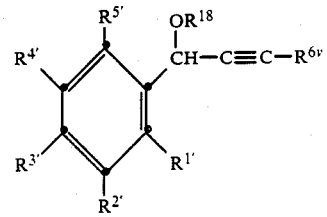

VII wherein $R^{1'}$, $R^{2'}$, $R^{3'}$, $R^{4'}$ and $R^{5'}$ are as defined above, $R^{6v}$ is a group of formula (a), (b) or (c) or a residue of the formula $$-C(R^{14})(R^{15})OR^{16'''} \quad\quad (f''')$$

in which $R^7$ and $R^{10}$ are different from hydrogen, $R^{14}$ and $R^{15}$ have the meanings given in formula 1 and $R^{16'''}$ has the meaning given for $R^{16'}$ in formula II, except, however, $R^{16'''}$ can additionally be a protecting group, and $R^{18}$ is a protecting group.

The oxidation in accordance with process variant (a) is effected under methods which are known and familiar to those skilled in the art of converting a hydroxy group into an oxo group. As the oxidation agent there can be used manganese dioxide (pyrolusite) in a suitable solvent which is inert under the reaction conditions, for example, a halogenated hydrocarbon such as methylene chloride or the like. The oxidation by means of manganese dioxide is conveniently effected in a temperature range of about 0° C. to about room temperature and takes about 10 minutes to about 20 hours, depending on the other reaction conditions. If $R^{6'}$ in formula II is a residue of formula (c) in which $R^{10}$ is hydrogen, then, depending on the reaction conditions, oxidation to a residue of formula (a) in which $R^7$ is hydrogen can be effected.

Suitable protecting groups in the compounds of formula III which are used as starting materials in process variant (b) are, of course, only those which can be cleaved off by methods which selectively remove these protecting groups without affecting other structural elements present in the molecule. The removal of the protecting group or groups from the compounds of formula III is effected according to methods known per se. As those skilled in the art will understand, the nature of the protecting group or groups must be taken into consideration when choosing the method to be used and care must be taken that only the protecting group or protecting groups is/are selectively removed without affecting other structural elements present in the molecule. Suitable O-protecting groups are, for example, readily cleavable acetal and ketal protecting groups such as methoxymethyl, methoxyethoxymethyl, 1-ethoxyethyl, 2-(trimethylsilyl)-ethoxymethyl, tetrahydro 2H-pyran-2-yl and the like; readily cleavable metal-organic groups, especially trialkylsilyl groups such as trimethylsilyl, t-butyldimethylsilyl and the like; readily cleavable aralkyl groups such as triphenylmethyl and the like; readily cleavable acyl groups such as acetyl and the like; etc. Suitable N-protecting groups are primarily readily cleavable acyl groups such as t-butyloxycarbonyl and the like.

Methods for the removal of the residues which have been mentioned hereinbefore as examples of protecting groups are described in the literature and are accordingly, familiar to any person skilled in the art. Thus, for example, the methoxymethyl group, the methoxyethoxymethyl group, the 1-ethoxyethyl group, the 2-(trimethylsilyl)-ethoxymethyl group, the tetrahydro-2H-pyran-2-yl group, the trimethylsilyl group, the t-butyldimethylsilyl group and the triphenylmethyl group can be cleaved off under acidic conditions, for example, by means of aqueous hydrochloric acid in an organic solvent which is inert under the reaction conditions, such as tetrahydrofuran. The tetrahydro-2H-pyran-2-yl group, the trimethylsilyl group and the t-butyldimethylsilyl group can, however, also be cleaved off conveniently by means of pyridinium p-toluene sulphonate in an organic solvent or solvent mixture which is inert under the reaction conditions, such as tetrahydrofuran/ethanol. The trimethylsilyl group and the t-butyldimethylsilyl group can also be cleaved off by means of a guaternary ammonium fluoride such as tetrabutylammonium fluoride in an organic solvent which is inert under the reaction conditions, such as tetrahydrofuran. The acetyl group can be cleaved off under mild alkaline conditions, for example, by means of dilute (about 2-5%) potassium hydroxide solution in an organic solvent which is inert under the reaction conditions, such as tetrahydrofuran. The cleavage of a t-butyloxycarbonyl group can be effected under acidic conditions, for example, by means of an aqueous acid or anhydrous trifluoroacetic acid.

Suitable leaving groups ($R^{17}$) in the compounds of formula IV which are used as starting materials in process variant (c) are primarily groups such as N-methoxy-N-methylamino and the like. The reaction of the compounds of formulae IV and V is effected in the presence of a strong base such as butyllithium, alkylmagnesium halides (e.g., ethylmagnesium bromide) and the like, in an organic solvent or solvent mixture which is inert under the reaction conditions, for example, in tetrahydrofuran/hexamethylphosphortriamide. Furthermore, the reaction is conveniently effected at a temperature of about $-80°$ to about room temperature and takes about 1 hour to about 3 hours.

The ester cleavage in accordance with process variant (d) is effected according to methods which are known and are familiar to those skilled in the art, and conveniently by hydrolysis using a strong inorganic base, for example, an alkali metal hydroxide such as potassium hydroxide or the like, in a suitable solvent system, for example, in water or aqueous tetrahydrofuran and the like. When $R^7$ is a benzyl residue which is readily cleavable under acidic conditions, such as 4-methoxybenzyl, 3,4-methylenedioxybenzyl, 2,4,6-trimethylbenzyl or the like, then the ester cleavage can also be effected by means of trifluoroacetic acid (in the presence or absence of a solvent such methylene chloride, anisole or the like). by means of formic acid, by means of hydrogen bromide in glacial acetic acid, or by means of analogous reagents.

The acylation in accordance with process variant (e) is also effected according to known methods. As the acylation agent there is used, for example, an acid halide which corresponds to the acyl residue to be introduced, such as acetyl chloride, 3,4,5-trimethoxybenzoyl chloride and the like. The acylation by means of such an acid halide is conveniently effected in the presence of a base, especially a tertiary organic base such as pyridine, triethylamine, N-methylpiperidine, 4-dimethylaminopyridine or the like. Suitable solvents are primarily halogenated hydrocarbons such as methylene chloride or the like. When pyridine is used as the base, then this base can simultaneously also serve as the solvent. If one or more of $R^1-R^5$ represents a hydroxy group and/or an amino group and/or a lower alkylamino group, then they are likewise acylated.

In accordance with process variant (f). an acetal or ketal group is converted into a carbonyl group. This is effected according to established methods which are familiar to those skilled in the art, and conveniently by means of aqueous perchloric acid or the like, in an organic solvent which is inert under the reaction conditions, such as dioxane or the like, at about room temperature and takes a few (for example, 2) hours.

The conversion of an acidic compound of formula I into a pharmaceutically usable salt can be carried out by treatment with a suitable base in a known manner. As such salts there are suitable not only those with cations derived from an inorganic base, e.g., potassium salts, sodium salts, calcium salts and the like, but also salts with organic bases such as ethylenediamine, monoethanolamine, diethanolamine and the like.

The conversion of a basic compound of formula I into a pharmaceutically usable salt can be carried out by treatment with a suitable acid. As such salts there are suitable not only those with inorganic acids such as hydrogen chloride, hydrogen bromide phosphoric acid, sulphuric acid and the like, but also salts with organic acids such as citric acid, malic acid, methanesulphonic acid, p-toluenesulphonic acid and the like.

The preparation of compounds of formula II in accordance with process variant (aa) is effected in the presence of a strong base such as butyllithium, alkylmagnesium halides (e.g., ethylmagnesium bromide) and the like, in an organic solvent or solvent mixture which is inert under the reaction conditions, for example, in tetrahydrofuran/n-hexane, tetrahydrofuran/diethyl ether/n-hexane and the like. The reaction temperature is preferably in the range from about $-120°$ to about room temperature, with the choice of the reaction temperature depending, inter alia, on the solvent or solvent mixture which is used. The reaction time is about 1-2 hours. The compounds of formula Va can be used in free form or in the form of reactive derivatives, conveniently in the form of tri-lower-alkylsilyl derivatives, such as trimethylsilyl derivatives. Examples of suitable compounds of formula Va or reactive derivatives thereof are: 1-(1-ethoxyethoxy)-2-propyne, methyl propiolate, propiolic acid, 3,3-diethoxy-1-propyne, 3-butyn-2-ol, ethyl propiolate. 1-[(3-methyl-2-butenyl)oxy]-2-propyne, triethyl 3-trimethylsilyl-orthopropiolate, and so forth.

Suitable protecting groups ($R^{18}$) in the compounds of formula VII which are used as starting materials in accordance with process variant (bb) are primarily readily cleavable metal-organic groups such as trimethylsilyl, t-butyldimethylsilyl and the like. Such residues are conveniently cleaved off by means of aqueous acid, for example, aqueous hydrochloric acid, in an organic solvent which is inert under the reaction conditions, such as ethyl acetate, dioxane or the like. The cleavage of such groups can, however, also be effected by means of pyridinium p-toluenesulphonate or a quaternary ammonium fluoride such as tetrabutylammonium fluoride.

The preparation of the starting materials of formula III can be carried out by analogy to the preparation of the corresponding compounds of formula I.

The starting materials of formulae IV, V and VI are available or can be prepared readily according to methods which are known to those skilled in the art. Moreover, many of the Examples hereinafter contain detailed information concerning the preparation of certain compounds of formula V.

The starting materials of formula VII can be prepared, for example, by reacting a compound of the formula

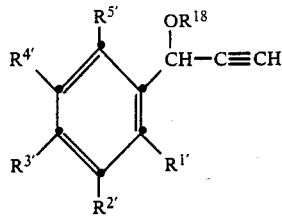

VIII wherein $R^{1'}$, $R^{2'}$, $R^{3'}$, $R^{4'}$, $R^{5'}$ and $R^{18}$ are as defined above,
in the presence of a strong base such as n-butyllithium or the like, in an organic solvent or solvent mixture which is inert under the reaction conditions, such as ether/n-hexane, tetrahydrofuran/n-hexane or the like, with a compound of the formula $$X - R^{6iv} \qquad IX$$

wherein $R^{6iv}$ has the above meaning and X is a leaving group (especially chlorine),
for example, with butyl chloroformate, N,N-dimethylcarbamoyl chloride or the like. The preparation of the starting materials of formula VIII is effected according to methods which are known to those skilled in the art from corresponding compounds of the formula

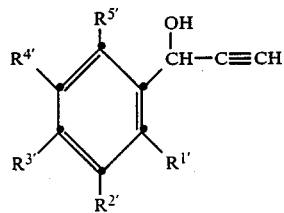

X wherein $R^{1'}$, $R^{2'}$, $R^{3'}$, $R^{4'}$ and $R^{5'}$ have the above meanings,
by introduction of the desired protecting group, for example, by means of trimethylsilyl chloride in the presence of n-butyllithium in ether/n-hexane, or by means of t butyldimethylsilyl chloride in the presence of 1,8-diazabicyclo[5.4.0]undec-7-ene in methylene chloride. The starting materials of formulae IX and X are available or can be prepared according to methods which are known.

As mentioned earlier, the compounds of formulae I and II as well as pharmaceutically acceptable salts of compounds of formula I possess valuable pharmacodynamic properties, as already described herein.

Representative compounds of formulae I and II were investigated with respect to their mucosa-protective and gastric acid secretion-inhibiting properties, as well as for their toxicity.

The experimental procedure described hereinafter was used to determine the mucosa-protective property:

The oral administration of absolute ethanol to male rats in a dosage of 1 ml per rat leads within 1 hour to bloody lesions of the mucous membrane of the stomach. Various dosages of the substances to be tested (suspended in 0.125% carboxymethycellulose) or of the vehicle alone (control) are administered to the rats orally (1 ml per rat) 30 minutes prior to the treatment with ethanol. One hour after the administration of the ethanol the animals are killed, their stomachs are investigated for the presence of lesions and the number and the total dimension of such lesions are determined. The $ID_{50}$ is that dosage of a test substance which reduces by 50% the number of lesions in comparison to the control group.

The test procedure described hereinafter was used to determine the gastric acid secretion-inhibiting activity:

The pylorus of male rats is ligated under slight ether narcosis in accordance with Shay et al., Gastroenterology 5. 43 (1945). The substances to be tested, suspended in 0.5% carboxymethylcellulose, are administered intraduodenally. Control animals are treated only with the vehicle. Five hours after the ligation the animals are killed, the volume and acidity of their gastric juice are determined and the values obtained are compared with those of control animals. The $ID_{50}$ is that dosage of a test substance which brings about a 50% decrease of the secretion in comparison to the control animals. In the following Table there are given for a series of representative compounds of formula I and for two compounds of formula II the results of the testing with respect to their mucosa-protective activity ("ethanol test") and to their gastric acid secretion-inhibiting activity. Moreover, this Table contains data concerning the acute toxicity ($LD_{50}$ in the case of single oral administration to mice).

| Compound | Ethanol Test ID 50 mg/kg p.o. | Gastric acid secretion-inhibition, ID 50 mg/kg i.d. | Toxicity LD 50 mg/kg p.o. |
| --- | --- | --- | --- |
| A | 1.2 | 42 | 625–1250 |
| B | 1.9 | 18 | 156–312 |
| C | 1.4 | — | 625–1250 |
| D | 2.1 | — | 625–1250 |
| E | 1.2 | — | 312–625 |
| F | 2.9 | — | >5000 |
| G | 2.1 | — | 1000–2000 |
| H | 2.2 | — | >5000 |
| I | 1.9 | — | 625–1250 |
| J | 2.3 | >100 | 1250–2500 |
| K | 3.4 | — | 500–1000 |
| L | 4.1 | 56 | 1000–2000 |
| M | 4.2 | — | 1250–2500 |
| N | 4.2 | >100 | >5000 |
| O | 2.8 | 28 | 312–625 |
| P | 0.9 | — | 80–156 |
| Q | 1.5 | — | 80–156 |
| R | 1.4 | — | 80–156 |
| S | 1.2 | — | 80–156 |
| T | 1.2 | — | 40–80 |
| U | 1.1 | — | 80–156 |
| V | 1.2 | 3.1 | 156–312 |
| W | 0.8 | 9 | 312–625 |
| X | 0.8 | 4.0 | 156–312 |
| Y | 1.0 | 2.7 | 156–312 |
| Aa | 1.4 | — | 312–625 |

| Compound | Ethanol Test ID 50 mg/kg p.o. | Gastric acid secretion-inhibition, ID 50 mg/kg i.d. | Toxicity LD 50 mg/kg p.o. |
|---|---|---|---|
| Bb | 4.0 | — | 625–1250 |

A = 3-[3,4-(Methylenedioxy)benzoyl]propiolic acid
B = 4-Hydroxy-1-(3,4,5-trimethoxyphenyl)-2-butyn-1-one
C = 3-(4-Methoxybenzoyl)propiolic acid
D = Methyl 3-(2,3,4-trimethoxybenzoyl)propiolate
E = Methyl 3-(4-hydroxybenzoyl)propiolate
F = 2-(2-Methoxyethoxy)ethyl 3-(3,4,5-trimethoxybenzoyl)-propiolate
G = 2-(2-Methoxyethoxy)ethyl 3-(4-methoxybenzoyl)-propiolate
H = Methyl 3-(2,5-dimethoxybenzoyl)propiolate
I = 3-(2,5-Dimethoxybenzoyl)propiolic acid
J = 2-(2-Methoxyethoxy)ethyl 3-[3,4-(methylenedioxy)-benzoyl]propiolate
K = 3-(2,3,4-Trimethoxybenzoyl)propiolic acid
L = 3-(3,4,5-Trimethoxybenzoyl)propiolic acid
M = Methyl 3-(4-fluorobenzoyl)propiolate
N = Methyl 3-(3,4,5-trimethoxybenzoyl)propiolate
O = N,N-Dimethyl-3-(3,4,5-trimethoxybenzoyl)propiolamide
P = 1-(4-Fluorophenyl)-4-hydroxy-2-butyn-1-one
Q = 4-Hydroxy-1-(4-methylphenyl)-2-butyn-1-one
R = 4-(1-Ethoxyethoxy)-1-(4-fluorophenyl)-2-butyn-1-one
S = 1-(4-Chlorophenyl)-4-hydroxy-2-butyn-1-one
T = 4-Hydroxy-1-(4-methoxyphenyl)-2-butyn-1-one
U = 4-Hydroxy-1-[3,4-(methylenedioxy)phenyl]-2-butyn-1-one
V = 4-Hydroxy-1-(3,4,5-trimethoxyphenyl)-2-pentyn-1-one
W = (1-Ethoxyethoxy)-1-(2,3,4-trimethoxyphenyl)-2-butyn-1-one
X = 4-Hydroxy-1-(2,3,4-trimethoxyphenyl)-2-butyn-1-one
Y = 4-Hydroxy-1-[4-(methylthio)phenyl]-2-butyn-1-one
Aa = Methyl 4-hydroxy-4-[3,4-methylenedioxy)phenyl]-2-butynoate
Bb = 2-(2-methoxyethoxy)ethyl 4-hydroxy-4-(3,4,5-trimethoxyphenyl)-2-butynoate.

The compounds of formulae I and II and the pharmaceutically acceptable salts of compounds of formula I can be used as medicaments, for example, in the form of pharmaceutical preparations. Oral administration of such compounds can be in the form of solid pharmaceutical preparations such as tablets, coated tablets, dragees, hard gelatine capsules and soft gelatine capsules. Oral administration in the form of liquid preparations such as solutions, emulsions and suspensions, rectal administration, e.g., suppositories, or parenteral administration, e.g. in the form of injection solutions, are also encompassed within the practice of this invention.

The preparation of medicaments of this invention can be effected by mixing one or more of the compounds of formula I or II or of the pharmaceutically usable salts of the compounds of formula I and, if desired, one or more other therapeutically active substances with one or more therapeutically inert excipients.

For the preparation of tablets, coated tablets, dragees and hard gelatine capsules in particular, the compounds of formulae I and II and the pharmaceutically usable salts of compounds of formula I can be processed with pharmaceutically inert, inorganic or organic excipients. As such excipients there can be used for tablets, dragees and hard gelatine capsules materials such as lactose, maize starch or derivatives thereof, talc, stearic acid or its salts, and so forth. For the preparation of pharmaceutical preparations which are resistant to gastric fluids it is necessary to apply a gastric fluid-resistant (enteric) coating which can consist of, for example, hydroxypropylmethylcellulose phthalate or other suitable material, as those skilled in the art will understand.

Suitable excipients for soft gelatine capsules are, for example, vegetable oils, waxes, fats, semi-solid and liquid polyols, and so forth.

Suitable excipients for the preparation of solutions and syrups are, for example, water, polyols, saccharose, invert sugar, glucose, and the like.

Suitable excipients for suppositories are, for example, natural or hardened oils, waxes, fats, semi-liquid or liquid polyols and the like.

Suitable excipients for injection solutions are, for example, water, alcohols, polyols, glycerine, vegetable oils, and so forth.

The pharmaceutical preparations can contain, in addition, preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention the compounds of formulae I and II and the pharmaceutically usable salts of compounds of formula I can be used in the control or prevention of illnesses, for example in the control or prevention of gastric ulcers and/or duodenal ulcers. The dosage can vary and, of course, will be fitted to the individual requirements in each particular case. In general, in the case of oral administration a daily administration of about 30–400 mg in single or divided doses, should be appropriate and in the case of intravenous administration a daily dosage of about 1–50 mg should be appropriate.

In the following Examples, which illustrate the present invention but which are not intended to be limiting, all temperatures are given in degrees Celsius.

EXAMPLE 1

(a) A solution of 20 g (0.36 mol) of 2-propyn-1-ol in 637 ml (6.66 mol) of ethyl vinyl ether was treated at 0° under argon with 1.27 ml (16.7 mmol) of trifluoroacetic acid and subsequently stirred at room temperature for 65 hours. 1.3 g of sodium carbonate were added, the reaction mixture was stirred at room temperature for a further 30 minutes and concentrated on a rotary evaporator. Distillation of the residue under reduced pressure Yielded 1-(1-ethoxyethoxy)-2-propyne of boiling point 55°/30 mmHg. MS: 127 (M-H) m/e.

(b) A solution of 8 g (62.4 mmol) of 1-(1-ethoxyethoxy)-2propyne in 135 ml of tetrahydrofuran was treated at −78° under argon with 39 ml of n-butyllithium (1.6M in hexane). The mixture was stirred at −40° for 30 minutes and then a solution of 12.3 g (62.4 mmol) of 2,3,4-trimethoxybenzaldehyde in 53 ml of tetrahydrofuran was added within 10 minutes. The reaction mixture was warmed to 0°, stirred at 0° for a further 1 hour and then treated with 100 ml of saturated ammonium chloride solution. The aqueous phase was extracted twice with ethyl acetate. The combined organic phases were washed in succession with saturated sodium chloride solution and with water, dried over magnesium sulphate and concentrated. The residue was purified by flash chromatography on 600 g of silica gel (elution agent ether/hexane 1:1). There was obtained 4-(1-ethoxyethoxy)-1- (2,3,4-trimethoxyphenyl)-2 butyn-1-ol as a yellow oil.

MS: 324 (M ) m/e

IR (film): 1600 1195 1467 1282 1096 cm (c) A solution of I2 g (37 mmol) of 4-(1-ethoxyethoxy)-1-(2,3,4-trimethoxyphenyl)-2-butyn-1-ol in 50 ml of methylene chloride was added dropwise at 0° to a suspension of 95.3 g (1.1 mol) of manganese dioxide in 150 ml of methylene chloride. The reaction mixture was stirred at 0° for 15 minutes, filtered over magnesium sulphate and concentrated. Chromatography of the residue over 300 g of silica gel (elution agent ether/hexane 1:1) yielded 4-(1-ethoxyethoxy)-1-(2,3,4-trimethoxyphenyl)-2-butyn-1-one as a yellow oil.

MS: 322 (M) m/e

IR (film): 2214, 1625, 1586, 1494, 1289 cm$^{-1}$

EXAMPLE 2

(a) A solution of 6 q (47 mmol) of 1-(1-ethoxyethoxy)-2-propyne in 100 ml of tetrahydrofuran was treated at −78° under argon with 29.2 ml of n-butyllithium (1.6M in hexane). The mixture was stirred at −40° for 30 minutes and then a solution of 6.6 g (47 mmol) of 1-chlorobenzaldehyde in 11 ml of tetrahydrofuran was added within 10 minutes. The reaction mixture was warmed to 0°, stirred at 0° for a further 1 hour and then treated with 80 ml of saturated ammonium chloride solution. The aqueous phase was extracted twice with ethyl acetate. The combined organic phases were washed in succession with saturated sodium chloride solution and with water, dried over magnesium sulphate and concentrated. The residue was purified by flash chromatography on 500 g of silica gel (elution agent ether/ hexane 1:1. There was obtained 4-(1-ethoxyethoxy)-1-(4- chlorophenyl) 2-butyn-I ol as an oil.

MS: 253 (M CH$_3$) m/e

IR (film): 3105, 1596, 1490, 1128, 1088 cm$^{-1}$ (b) A solution of 7.1 g (26.4 mmol) of 4-(1-ethoxyethoxy)-1-(4-chlorophenyl)-2-butyn-1-ol in 40 ml of methylene chloride was added dropwise at 0° to a suspension of 68 g (0.78 mol) of manganese dioxide in 110 ml of methylene chloride. The reaction mixture was stirred at 0° for lo minutes, filtered over magnesium sulphate and concentrated. Chromatography of the residue on 300 g of silica gel (elution agent ether/hexane 1:1) yielded 4-(1-ethoxyethoxy) -1-(4-chlorophenyl)-2-butyn-1-one as an oil.

MS: 251 (M-CH$_3$) m/e

EXAMPLE 3

(a) A solution of 5 q (33 mmol) of 1-(1-ethoxyethoxy)-2-propyne in 84 ml of tetrahydrofuran was treated at −78° under argon with 24.4 ml of n-butyllithium (1.6M in hexane). The mixture was stirred at −40° for 30 minutes and then a solution of 4.6 ml (33 mmol) of 4-methylbenzaldehyde in 34 ml of tetrahydrofuran was added within 10 minutes. The reaction mixture was warmed to 0°, stirred at 0° for a further 1 hour and then treated with 60 ml of saturated ammonium chloride solution. The aqueous phase was extracted twice with ether. The combined organic phases were washed in succession with saturated sodium chloride solution and with water, dried over magnesium sulphate and concentrated. The residue was purified by chromatography on 500 g of silica gel (elution agent ether/hexane 1:I). There was obtained 4-(1-ethoxyethoxy)-1-(4-methylphenyl)-2- butyn-I-ol.

MS: 247 (M-H) m/e

IR (film): 1512. 1128, 1086 cm$^{-1}$ (b) A solution of 6.7 g (27 mmol) of 4 (1-ethoxyethoxy)-1-(4-methylphenyl)-2-butyn-1-ol in 40 ml of methylene chloride was added dropwise at 0° to a suspension of 69 g (0.79 mol) of manganese dioxide in 110 ml of methylene chloride. The reaction mixture was stirred at 0° for 10 minutes, filtered over magnesium sulphate and concentrated. Chromatography of the residue on 300 g of silica gel (elution agent ether/hexane 1:1) yielded 4-(1-ethoxyethoxy)-1-(4-methylphenyl)-2-butyn-1-one as a yellow oil.

MS: 231 (M-CH$_3$) m/e

IR (film): 2228, 1646, 1605, 1287 cm$^{-1}$

EXAMPLE 4

(a) A solution of 8 g (62.4 mmol) of 1 (1-ethoxyethoxy)-2-propyne in 134 ml of tetrahydrofuran was treated at −78° under argon with 39 ml of n-butyllithium (1.6M in hexane). The mixture was stirred at −40° for 30 minutes and then a solution of 6.6 ml (62 mmol) of 4-fluorobenzaldehyde in 54 ml of tetrahydrofuran was added within 10 minutes. The reaction mixture was warmed to 0°, stirred at 0° for a further 1 hour and then treated with 100 ml of saturated ammonium chloride solution. The aqueous phase was extracted twice with ethyl acetate. The combined organic phases were washed in succession with saturated sodium chloride solution and with water, dried over magnesium sulphate and concentrated. The residue was purified by chromatography on 600 g of silica gel (elution agent ether/hexane 1:1). There was obtained 4-(1-ethoxyethoxy)-1-(4-fluorophenyl)-2- butyn-1-ol as an oil.

MS: 251 (M-H) m/e

IR (film): 3408, 1604, 1508 cm$^{-1}$ (b) A solution of 9.3 g (37 mmol) of 4-(1-ethoxyethoxy)-1-(4-fluorophenyl)-2-butyn-1-ol in 50 ml of methylene chloride was added dropwise at 0° to a suspension of 95 g (1.1 mol) of manganese dioxide in 150 ml of methylene chloride. The reaction mixture was stirred at 0° for 10 minutes, filtered over magnesium sulphate and concentrated. Chromatography of the residue on 300 g of silica gel (elution agent ether/hexane 1:1) yielded 4 (I-ethoxyethoxy) 1-(4-fluorophenyl)-2-butyn 1-one as an oil.

MS: 235 (M-CH$_3$) m/e

IR (film): 2228, 1651, 1596, 1504 cm$^{-1}$

EXAMPLE 5

(a) A solution of 6 g (47 mmol) of 1-(1-ethoxyethoxy)-2-propyne in 100 ml of tetrahydrofuran was treated at −78° under argon with 29.2 ml of n-butyllithium (1.6M in hexane). The mixture was stirred at −40° for 30 minutes and then a solution of 5.7 ml (47 mmol) of 4-methoxybenzaldehyde in 41 ml of tetrahydrofuran was added within 10 minutes. The reaction mixture was warmed to 0°, stirred at 0° for a further 1 hour and then treated with 80 ml of saturated ammonium chloride solution. The aqueous phase was extracted twice with ethyl acetate. The combined organic phases were washed in succession with saturated sodium chloride solution and with water dried over magnesium sulphate and concentrated. The residue was purified by flash chromatography on 500 g of silica gel (elution agent ether/hexane 1:1). There was obtained 4-(1-ethoxyethoxy)-1-(4-methoxyphenyl)-2-butyn-1-ol as an oil.

MS: 264 (M+) m/e

IR (film): 3412, 1811, 1512, 1250 cm$^{-1}$ (b) A solution of 7.6 g (29 mmol) of 4-(1-ethoxyethoxy)-1-(4-methoxyphenyl)-2-butyn-1-ol in 56 ml of methylene chloride was added dropwise at 0° to a suspension of 74 g (0.85 mol) of manganese dioxide in 100 ml of methylene chloride. The reaction mixture was stirred at 0° for 10 minutes, filtered over magnesium sulphate and concentrated. Chromatography of the residue on 300 g of silica gel (elution agent ether/hexane 1:1) Yielded 4-(1-ethoxyethoxy) -1-(4-methoxyphenyl)-2-butyn-1-one as an oil.

MS: 247 (M-CH$_3$) m/e

IR (film): 2229, 1642, 1598, 1509, 1259 cm$^{-1}$

EXAMPLE 6

(a) A solution of 8 g 62.4 mmol) of 1- 1-ethoxyethoxy)-2-propyne in 134 ml of tetrahydrofuran was treated at −78° under argon with 39 ml of n-butyllithium (1.6M in hexane). The mixture was stirred at −10° for 30 minutes and then a solution of 9.4 ml (62.4 mmol) of 3.1-methylenedioxybenzaldehyde in 54 ml of tetrahydrofuran was added within 10 minutes. The reaction mixture was warmed to 0°, stirred at 0° for a further 1 hour and then treated with 100 ml of saturated ammonium chloride solution. The aqueous phase was extracted twice with ethyl acetate. The combined organic phases were washed in succession with saturated sodium chloride solution and with water, dried over magnesium sulphate and concentrated. The residue was purified by chromatography on 500 g of silica gel (elution agent ether/hexane 1:1). There was obtained 4-(1-ethoxyethoxy)-1-[3.4-(methylenedioxy)phenyl]2-butyn-1-ol as an oil.

MS: 278 (M+) m/e
IR (film); 3410, 1487, 1448, 1247 cm$^{-1}$ (b) A solution of 10.9 g 39.2 mmol) of 4-(1-ethoxyethoxy)-1-[3,4-(methylenedioxy)phenyl]-2-butyn-1-ol in 63 ml of methylene chloride was added dropwise at 0° to a suspension of 101 g (1.16 mol) of manganese dioxide in 150 ml of methylene chloride. The reaction mixture was stirred at 0° for 10 minutes, filtered over magnesium sulphate and concentrated. Chromatography of the residue on 300 g of silica gel (elution agent ether/hexane 1:1) yielded 4-(1-ethoxyethoxy)-1-[3,4-(methylenedioxy)phenyl]2-butyn-1-one as an oil.

MS: 276 (M+) m/e
IR (film); 2230, 1640, 1602, 1289 cm$^{-1}$

EXAMPLE 7

(a) A solution of 16 g (124.8 mmol) of 1-(1-ethoxyethoxy)-2-propyne in 270 ml of tetrahydrofuran was treated at −78° under argon with 78 ml of n-butyllithium (1.6M in hexane). The mixture was stirred at −40° for 30 minutes and then a solution 7.62 g (62.4 mmol) of 4-hydroxybenzaldehyde in 53 ml of tetrahydrofuran was added within 10 minutes. The reaction mixture was warmed to 0°, stirred at 0° for a further 1 hour and then treated with 100 ml of saturated ammonium chloride solution. The aqueous phase was extracted twice with ethyl acetate. The combined organic phases were washed in succession with saturated sodium chloride solution and with water, dried over magnesium sulphate and concentrated. The residue was purified by flash chromatography on 600 g of silica gel (elution agent ether/hexane 1:1). There was obtained 4-(1 ethoxyethoxy)-(4-hydroxyphenyl)-2-butyn-l-ol as an oil.

MS: 250 (M+) m/e
IR (film): 3268, 1614, 1516, 1276 cm$^{-1}$ (b) A solution of 8.6 g (34.4 mmol) of 4-(1-ethoxyethoxy)-1-(4-hydroxyphenyl)-2-butyn-I-ol in 50 ml of methylene chloride was added dropwise ar 0° to a suspension of 89 g (1.02 mol) of manganese dioxide in 150 ml of methylene chloride. The reaction mixture was stirred at 0° for 15 minutes, filtered over magnesium sulphate and concentrated. Flash chromatography of the residue on 200 g of silica gel (elution agent ether/hexane 1:1) yielded 4-(1-ethoxyethoxy)-1-(4-hydroxyphenyl)-2-butyn-1 one as an oil.

MS: 233 (M-CH$_3$) m/e
IR (film): 3267, 2232, 1629, 1577, 1512 cm$^{-1}$

EXAMPLE 8

(a) A solution of 8 g (62.4 mmol) of 1-(1-ethoxyethoxy)-2-propyne in 135 ml of tetrahydrofuran was treated at −78° under argon with 39 ml of n-butyllithium (1.6M in hexane). The mixture was stirred at −40° for 30 minutes and then a solution of 8.11 ml (62.4 mmol) of 4-(methylthio)benzaldehyde in 53 ml of tetrahydrofuran was added within 10 minutes. The reaction mixture was warmed to 0°, stirred at 0° for a further 1 hour and then treated with 100 ml of saturated ammonium chloride solution. The aqueous phase was extracted twice with ethyl acetate. The combined organic phases were washed in succession with saturated sodium chloride solution and with water, dried over magnesium sulphate and concentrated. The residue was purified by flash chromatography on 600 g of silica gel (elution agent ether/hexane 1:1). There was obtained 4-(1-ethoxyethoxy)-1- [4-(methylthio)phenyl]-2-butyn-1 ol as an oil.

MS: 280 (M+) m/e
IR (film): 3407, 2116, 1598, 1192 cm$^{-1}$ (b) A solution of 10.9 g (3B.9 mmol) of 4-(1-ethoxyethoxy)-1-[4-(methylthio)phenyl]-2-butyn-1-ol in 50 ml of methylene chloride was added dropwise at 0° to a suspension of 100 g (1.15 mol) of manganese dioxide in 170 ml of methylene chloride. The reaction mixture was stirred at 0° for 15 minutes, filtered over magnesium sulphate and concentrated. Flash chromatography of the residue on 200 g of silica gel (elution agent ether/hexane 1:1) yielded 4-(1-ethoxyethoxy) 1-[4-(methylthio)phenyl]-2-butyn-1-one as an oil.

MS: 278 (M+) m/e
IR (film): 2230, 1640, 1588, 1105 cm$^{-1}$

EXAMPLE 9

A solution of 8.3 g (27.6 mmol) of 4-1-ethoxyethoxy) 1-(2,3,4-trimethoxyphenyl)-2 butyn-1-one in 95 ml of tetrahydrofuran was treated at room temperature with 27.5 ml of 2N hydrochloric acid, whereupon the mixture was stirred for 30 minutes. The reaction mixture was then extracted twice with ethyl acetate. The combined organic phases were washed in succession with saturated sodium carbonate solution and with water, dried over magnesium sulphate and concentrated. Crystallization of the residue from ethyl acetate/hexane yielded 4-hydroxy-1-(2,3,4- trimethoxyphenyl)-2-butyn-1-one of melting point 82°–83°.

EXAMPLE 10

A solution of 6.7 g (25 mmol) of 4-(1-ethoxyethoxy)-1-(4-chlorophenyl)-2-butyn-1-one in 90 ml of tetrahydrofuran was treated at room temperature with 25 ml of 2N hydrochloric acid, whereupon the mixture was stirred for 30 minutes. The reaction mixture was then extracted twice with ethyl acetate. The combined organic phases were washed in succession with saturated sodium carbonate solution and with water, dried over magnesium sulphate and concentrated. Crystallization of the residue from ethyl acetate/hexane yielded 1-(4-chlorophenyl)-4-hydroxy-2-butyn-1-one of melting point 74°.

EXAMPLE 11

A solution of 5.7 g (23 mmol) of 4-(1-ethoxyethoxy)-1-(4-methylphenyl)-2-butyn-1-one in 80 ml of tetrahydrofuran was treated at room temperature with 23 ml of 2N hydrochloric acid, whereupon the mixture was stirred for 30 minutes. The reaction mixture was then extracted twice with ethyl acetate. The combined organic phases were washed in succession with saturated sodium carbonate solution and with water, dried over magnesium sulphate and concentrated. Crystallization of the residue from ethyl acetate/hexane yielded 4-hydroxy-1-(4-methylphenyl)-2-butyn-1-one of melting point 74°.

EXAMPLE 12

A solution of 7.3 g (29 mmol) of 4-(1-ethoxyethoxy)-1-(4-fluorophenyl)-2-butyn-1-one in 100 ml of tetrahydrofuran was treated at room temperature with 29 ml of 2N hydrochloric acid, whereupon the mixture was stirred for 30 minutes. The reaction mixture was then extracted twice with ethyl acetate. The combined organic phases were washed in succession with saturated sodium carbonate solution and with water, dried over magnesium sulphate and concentrated. Crystallization of the residue from ethyl acetate/ hexane yielded 1-(4-fluorophenyl)-4-hydroxy-2-butyn-1-one of melting point 63°.

EXAMPLE 13

A solution of 7.3 g (27.8 mmol) of 4-(1-ethoxyethoxy)-1-(4-methoxyphenyl)-2-butyn-1-one in 95 ml of tetrahydrofuran was treated at room temperature with 28 ml of 2N hydrochloric acid, whereupon the mixture was stirred for 30 minutes. The reaction mixture was then extracted twice with ethyl acetate. The combined organic phases were washed in succession with saturated sodium carbonate solution and with water, dried over magnesium sulphate and concentrated. Crystallization of the residue from methylene chloride/hexane yielded 4-hydroxy-1-(4-methoxyphenyl)-2- -butyn-1-one of melting point 84°-85°.

EXAMPLE 14

A solution of 5.2 g (18.8 mmol) of 4-(1-ethoxyethoxy)-1-[3, 4-(methylenedioxy)phenyl]-2-butyn-1-one in 65 ml of tetrahydrofuran was treated at room temperature with 18.7 ml of 2N hydrochloric acid, whereupon the mixture was stirred for 30 minutes. The reaction mixture was then extracted twice with ethyl acetate. The combined organic phases were washed in succession with saturated sodium carbonate solution and with water, dried over magnesium sulphate and concentrated. Crystallization of the residue from ethyl acetate/hexane yielded 4-hydroxy-1 [3,4(methylenedioxy)phenyl]-2-butyn-1-one of melting point 91°-93°.

EXAMPLE 15

A solution of 10.2 g (36.6 mmol) of 4-(1-ethoxyethoxy) -1-[4-methylthio)phenyl]-2-butyn-1-one in 126 ml of tetrahydrofuran was treated at room temperature with 36.5 ml of 2N hydrochloric acid, whereupon the mixture was stirred for 30 minutes. The reaction mixture was then extracted twice with ethyl acetate. The combined organic phases were washed in succession with saturated sodium carbonate solution and with water, dried over magnesium sulphate and concentrated. Chromatography of the residue on 350 g of silica gel (elution agent methylene chloride/ethyl acetate 9:1) and subsequent crystallization from ethyl acetate/hexane yielded 4 hydroxy-1-[4-(methylthio)phenyl]--2-butyn-1-one of melting point 73°-74°.

EXAMPLE 16

44.6 ml of n-butyllithium solution (1.6M in hexane) were added to a solution of 10.0 g (71.3 mmol) of 3-[(tetrahydro-2H-pyran-2-yl)oxy]1-propyne in 150 ml of absolute tetrahydrofuran at −78°. The reaction mixture was stirred at −40° for 30 minutes and then treated with 14.0 g (71.3 mmol) of 3,4,5-trimethoxybenzaldehyde in 50 ml of tetrahydrofuran. The reaction mixture was subsequently stirred at 0° for 1 hour and then treated with 100 ml of saturated ammonium chloride solution and 200 ml of ether. The aqueous phase was extracted twice with ether, whereupon the combined organic phases were dried over magnesium sulphate and the solvent was distilled off. The residue was dissolved in 150 ml of methylene chloride and added dropwise at 0° to a suspension of 186 g of manganese dioxide in 300 ml of methylene chloride. The reaction mixture was stirred at room temperature for 30 minutes, filtered over magnesium sulphate and evaporated. The residue was dissolved in 300 ml of tetrahydrofuran/ethanol (1:1) and treated with 2.4 g of pyridinium p-toluenesulphonate. The mixture was stirred at room temperature for 24 hours, 100 ml of water and 200 ml of ether were then added, the aqueous phase was extracted twice with ether, the combined organic phases were dried over magnesium sulphate and the solvent was distilled off. Crystallization from ethyl acetate/hexane yielded 4-hydroxy 1-(3, 4, 5-trimethoxyphenyl)-2-butyn 1-one of melting point 104°-105°.

EXAMPLE 17 a) A solution of 3.4 ml (40 mmol) of methyl propiolate in 30 ml of tetrahydrofuran was treated at −78° under argon with 25 ml of n-butyllithium (1.6M in hexane). The mixture was stirred at −78° for 10 minutes and then a solution of 7.85 g (40 mmol) of 2,3,4-trimethoxybenzaldehyde in 40 ml of tetrahydrofuran was added within 10 minutes. The reaction mixture was brought to room temperature, stirred for 15 minutes and treated with 60 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 500 g of silica gel (elution agent methylene chloride/ethyl acetate 9:1). There was obtained methyl 4-hydroxy-4-(2,3,4- trimethoxyphenyl)-2-butynoate as a red oil.

MS: 280 (M+) m/e b) A solution of 7 g (25 mmol) of methyl 4-hydroxy-4-(2,3,4-trimethoxyphenyl)-2-butynoate in 40 ml of methylene chloride was added dropwise at 0° to a suspension of 62 g (0.71 mol) of manganese dioxide in 140 ml of methylene chloride. The reaction mixture was stirred at 0° for 1 hour, filtered over magnesium sulphate and concentrated. Crystallization of the residue from ethyl acetate/hexane yielded methyl 3-(2, 3, 4-trimethoxybenzoyl)propiolate of melting point 74°.

EXAMPLE 18 a) 71.6 ml of n-butyllithium solution (1.6M in hexane) were added to a solution of 9.6 ml (0.115 mol) of methyl propiolate in 195 ml of tetrahydrofuran/ether/hexane (4:2:1) at −110°. The mixture was stirred at −110° for 20 minutes, whereupon 15.0 g (76.4 mmol) of 3,4,5-trimethoxybenzaldehyde in 15 ml of ether were added within 20 minutes. The reaction mixture was stirred at −78° for a further 90 minutes, then brought slowly to room temperature and thereupon treated with 100 ml of saturated ammonium chloride solution. The aqueous phase was extracted twice with ethyl acetate. The combined organic phases were dried over magnesium sulphate and evaporated. Chromatography on silica gel with ethyl acetate/hexane (1:2) yielded methyl 4-hydroxy-4-(3,4,5-trimethoxyphenyl)-2-butynoate.

MS: 280 (H+) m/e

IR (film): 2237(m), 1717(s), 1595(s), 1225(s), 1126(s), 1003(m).

b) A solution of 6.84 g (24.4 mmol) of methyl 1-hydroxy-4-(3,1,5-trimethoxyphenyl) 2-butynoate in 10 ml of methylene chloride was added dropwise at 0° to a suspension of 63.7 g (0.73 mol of manganese dioxide in 130 ml of methylene chloride. The reaction mixture was stirred at 0° for 1 hour, filtered over magnesium sulphate and evaporated. Crystallization of the residue from ethyl acetate/hexane yielded methyl 3-(3, 4, 5-trimethoxybenzoyl) propiolate of melting point 97°.

EXAMPLE 19 a) A solution of 5 ml (60 mmol) of methyl propiolate in 60 ml of tetrahydrofuran was treated at −78° under argon with 37.5 ml of n-butyllithium (1.6M in hexane). The mixture was stirred at −78° for 10 minutes and then a solution of 9 g 60 mmol) of 3,4-methylenedioxybenzaldehyde in 60 ml of tetrahydrofuran was added within 30 minutes. The reaction mixture was stirred at −78° for a further 20 minutes, then brought to room temperature and treated with 80 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 500 g of silica gel (elution agent methylene chloride/ethyl acetate 9:1). There was obtained methyl 4-hydroxy-4-[3,4-(methylenedioxy)phenyl]-2-butynoate as a brown oil.

MS: 234 (M+) m/e (b) A solution cf 7.3 g (31 mmol) of methyl 4-hydroxy-4[3,4-(methylenedioxy)phenyl]-2-butynoate in 80 ml of methylene chloride was added dropwise at 0° to a suspension of 77 g (0.89 mol) of manganese dioxide in 150 ml of methylene chloride. The reaction mixture was stirred at 0° for 30 minutes, filtered over magnesium sulphate and concentrated. Crystallization of the residue from ether/hexane yielded methyl 3-[3,4-(methylenedioxy) benzoyl)-propiolate of melting point 95°–97°.

EXAMPLE 20

(a) A solution of 5 ml (60 mmol) of methyl propiolate in 60 ml of tetrahydrofuran was treated at −78° under argon with 37.5 ml of n-butyllithium (1.6M in hexane). The mixture was stirred at −78° for 10 minutes and then a solution of 7.3 ml (60 mmol) of 4-methoxybenzaldehyde in 70 ml of tetrahydrofuran was added within 30 minutes. The reaction mixture was stirred at −78° for a further 20 minutes, then brought to room temperature and treated with 80 ml of saturated ammonium chloride solution. The aqueous phase was extracted twice with ether. The combined organic phases were washed in succession with saturated sodium chloride solution and with water dried over sodium sulphate and concentrated. The residue was purified by flash chromatography on 700 g of silica gel (elution agent methylene chloride/ethyl acetate 9:1). There was obtained methyl 4-hydroxy-4-(4-methoxyphenyl)-2-butynoate as a red oil.

MS: 220 (M+) m/e (b) A solution of 75 g (34 mmol) of methyl 4-hydroxy-4-(4-methoxyphenyl)-2-butynoate in 100 ml of methylene chloride was added dropwise at 0° to a suspension of 84.4 g (0.97 mol) of manganese dioxide in 150 ml of methylene chloride. The reaction mixture was stirred at 0° for 30 minutes, filtered over magnesium sulphate and concentrated. Crystallization of the residue from ether/hexane yielded methyl 3-(4-methoxybenzoyl)-propiolate of melting point 68°.

EXAMPLE 21

(a) A solution of 2.16 ml (25.6 mmol) of methyl propiolate in 30 ml of tetrahydrofuran was treated at −78° under argon with 15.6 ml of n-butyllithium (1.6M in hexane). The mixture was stirred at −78° for 10 minutes and then a solution of 4.1 g (25.6 mmol) of 5,6,7,8-tetrahydronaphthyl-2-carboxaldehyde in 40 ml of tetrahydrofuran was added within 10 minutes. The reaction mixture was stirred at −78° for a further 10 minutes then brought to room temperature and treated with 100 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 500 g of silica gel (elution agent methylene chloride/ethyl acetate 9:1). There was obtained methyl 4-hydroxy-4-[2-(5,6,7,8-tetra-hydronaphthyl)]-2-butynoate as a red oil.

MS: 244 (M+), 229 (base peak) m/e (b) A solution of 3.3 g (13.5 mmol) of methyl 4-hydroxy-4[2-(5,6,7,8-tetrahydronaphthyl)]-2-butynoate in 100 ml of methylene chloride was added dropwise at 0° to a suspension of 35 g (0.4 mol) of manganese dioxide in 100 ml of methylene chloride. The reaction mixture was stirred at 0° for 20 minutes, filtered over magnesium sulphate and concentrated. The residue was purified by flash chromatography on 100 g of silica gel (elution agent methylene chloride/ethyl acetate 9:1). There was obtained methyl 3-[2-(5,6,7,8-tetrahydronaphthyl)carbonyl]propiolate as a yellow oil.

MS: 242 (M+), 131 (base peak) m/e

IR (film): 1723, 1648, 1602, 1494, 1268, 1248 cm$^{-1}$

EXAMPLE 22

(a) A solution of 2.8 ml (32 mmol) of methyl propiolate in 60 ml of tetrahydrofuran was treated at −78° under argon with 20 ml of n-butyllithium (1.6M in hexane). The mixture was stirred at −78° for 10 minutes and then a solution of 4.7 g (32 mmol) of 5-formylindane in 80 ml of tetrahydrofuran was added within 15 minutes. The reaction mixture was stirred at −78° for a further 10 minutes, then brought to room temperature and treated with 60 ml of saturated ammonium chloride solution. The aqeuous phase was extracted twice with ether. The combined organic phases were washed in succession with saturated sodium chloride solution and with water, dried over sodium sulphate and concentrated. The residue was purified by flash chromatography on 500 g of silica gel (elution agent methylene chloride/ethyl acetate 9:1). There was obtained methyl 4-hydroxy-4-(5-indanyl)-2-butynoate as a yellow oil.

MS: 230 (M+), 215 (base peak) m/e (b) A solution of 6 g (26 mmol) of methyl 4-hydroxy-4-(5-indanyl)-2-butynoate in 200 ml of methylene chloride was added dropwise at 0° to a suspension of 68 g (0.78 mol) of manganese dioxide in 200 ml of methylene chloride. The reaction mixture was stirred at 0° for 20 minutes, filtered over magnesium sulphate and concentrated. The residue was purified by flash chromatography on 500 g of silica gel (elution agent methylene chloride/ethyl acetate 9:1). There was obtained methyl 3-(5-indanylcarbonyl)propiolate as a yellow oil.

MS: 228 (M+), 117 (base peak) m/e

EXAMPLE 23

(a) A solution of 7.5 ml (90 mmol) of methyl propiolate in 80 ml of tetrahydrofuran was treated at −78° under argon 10 with 56.3 ml of n-butyllithium (1.6M in hexane). The mixture was stirred at −78° for 10 minutes and then a solution of 8.4 ml (80 mmol) of 4-fluorobenzaldehyde in 80 ml of tetrahydrofuran was added within 40 minutes. The reaction mixture was stirred at −78° for a further 20 minutes, then brought to room temperature and treated with 80 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 800 g of silica gel (elution agent methylene chloride/ethyl acetate 9:1). There was obtained methyl 4-(4-fluorophenyl)-4-hydroxy-2-butynoate as a yellow oil.

MS: 208 (M+), 123 (base peak) m/e (b) A solution of 7.5 g (36 mmol) of methyl 4-(4-fluorophenyl)-4-hydroxy-2-butynoate in 100 ml of methylene chloride was added dropwise at 0° to a suspension of 89.3 g (1.03 mol) of manganese dioxide in 150 ml of methylene chloride. The reaction mixture was stirred at 0° for 30 minutes filtered over magnesium sulphate and concentrated. Crystallization of the residue from ether/hexane yielded methyl 3-(4-fluorobenzoyl)propiolate of melting point 62°–63°.

EXAMPLE 24

(a) A solution of 8.36 ml (0.1 mol) of methyl propiolate in 100 ml of tetrahydrofuran was treated at −78° under argon with 68.8 ml of n-butyllithium (1.6M in hexane). The mixture was stirred at −78° for 10 minutes and then a solution of 14.06 g (0.1 mol) of 4-chlorobenzaldehyde in 100 ml of tetrahydrofuran was added within 40 minutes. The reaction mixture is stirred at −78° for a further 20 minutes, then brought to room temperature and treated with 100 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 1000 g of silica gel (elution agent methylene chloride/ethyl acetate 9:1). There was obtained methyl 4-(4-chlorophenyl)-4-hydroxy-2-butynoate as a red oil.

MS: 224 (M+), 53 (base peak) m/e (b) A solution of 4 g (17.8 mmol) of methyl 4-(4-chlorophenyl)-4-hydroxy-2-butynoate in 50 ml of methylene chloride was added dropwise at 0° to a suspension of 45 g (0.52 mol) of manganese dioxide in 100 ml of methylene chloride. The reaction mixture was stirred at 0° for 30 minutes filtered over magnesium sulphate and concentrated. Crystallization of the residue from ether/hexane fielded methyl 3-(4-chlorobenzoyl)propiolate of melting point 47°–48°.

EXAMPLE 25

(a) A solution of 8.4 ml (0.1 mol) of methyl propiolate in 100 ml of tetrahydrofuran was treated at −78° under argon with 68.8 ml of n-butyllithium (1.6M in hexane). The mixture was stirred at −78° for 10 minutes and then a solution of 11.8 ml (0.1 mol) of 4-methylbenzaldehyde in 100 ml of tetrahydrofuran was added within 40 minutes. The reaction mixture was stirred at −78° for a further 20 minutes, then brought to room temperature and treated with 100 ml of saturated ammonium chloride solution The aqueous phase was extracted twice with ether. The combined organic phases were washed in succession with saturated sodium chloride solution and with water, dried over sodium sulphate and concentrated. The residue was purified by flash chromatography on 1000 g of silica gel (elution agent methylene chloride/ethyl acetate 9:1). There was obtained methyl 4-hydroxy-4-(4-methylphenyl)-2-butynoate as a yellow oil.

MS: 204 (M+), 189 (base peak) m/e (b) A solution of 8.1 g (39.7 mmol) of methyl 4-hydroxy-4-(4-methylphenyl)-2-butynoate in 100 ml of methylene chloride was added dropwise at 0° to a suspension of 97 g (1.1 mol) of manganese dioxide in 200 ml of methylene chloride. The reaction mixture was stirred at 0° for 30 minutes, filtered over magnesium sulphate and concentrated. Crystallization of the residue from ether/hexane yielded methyl 3-(4-methylbenzoyl)propiolate of melting point 55°–56°.

EXAMPLE 26

(a) A solution of 6.7 ml (80 mmol) of methyl propiolate in 80 ml of tetrahydrofuran was treated at −78° under argon with 53.1 ml of n-butyllithium (1.6M in hexane). The mixture was stirred at −78° for 10 minutes and then a solution of 11.94 g (80 mmol) of 4-dimethylaminobenzaldehyde in 80 ml of tetrahydrofuran was added within 30 minutes. The reaction mixture was stirred at −78° for a further 20 minutes then brought to room temperature and treated with 120 ml of saturated ammonium chloride solution. The aqueous phase was extracted twice with ether, the combined organic phases were washed in sequence with saturated sodium chloride solution and with water, dried over sodium sulphate and concentrated. The residue was purified by flash chromatography on 1000 g of silica gel (elution agent methylene chloride/ethyl acetate 9:1). There was obtained methyl 4-[4-(dimethylamino)phenyl]-4-hydroxy-2-butynoate as a red oil.

MS: 233 (M+), 216 (base peak) m/e (b) A solution of 9.1 g (39 mmol) of methyl 4-[4(dimethylamino)phenyl]-4-hydroxy-2-butynoate in 100 ml of methylene chloride was added dropwise at 0° to a suspension of 96.7 g (1.1 mol) of manganese dioxide in 200 ml of methylene chloride The reaction mixture was stirred at 0° for 1 hour filtered over magnesium sulphate and concentrated. Crystallization of the residue from methylene chloride/ether fielded methyl 3-[4-(dimethylamino)benzoyl]-propiolate of melting point 112°–114°.

EXAMPLE 27

(a) A solution of 8.4 ml (0.1 mol) of methyl propiolate in 100 ml of tetrahydrofuran was treated at −78° under argon with 69 ml of n-butyllithium (1.6M in hexane). The mixture was stirred at −78° for 10 minutes and then a solution of 13 ml (0.1 mol) of 4-(methylthio)benzaldehyde in 100 ml of tetrahydrofuran was added within 40 minutes. The reaction mixture was stirred at −78° for a further 20 minutes, then brought to room temperature and treated with 150 ml of saturated ammonium chloride solution. The aqueous phase was extracted twice with ether. The combined organic phases were washed in succession with saturated sodium chloride solution and with water, dried over sodium sulphate and concentrated The residue was purified by flash chromatography on 1000 g of silica gel (elution agent methylene chloride/ether 4:1). There was obtained methyl 4-hydroxy-4-[4-(methylthio)phenyl]-2-butynoate as a red oil.

MS: 236 (M+) m/e (b) A solution of 11.6 g (49 mmol) of methyl 4-hydroxy-4-[4-(methylthio)phenyl]-2-butynoate in 300 ml of methylene chloride was added dropwise at 0° to a suspension of 124 g (1.42 mol) of manganese dioxide in 300 ml of methylene chloride. The reaction mixture was stirred at 0° for 2 hours filtered over magnesium sulphate and concentrated. Crystallization of the residue from ether/hexane yielded methyl 3-[4-(methylthio)-benzoyl]propiolate of melting point 74°–76°.

EXAMPLE 28

(a) A solution of 12.5 ml (0.15 mol) of methyl propiolate in 150 ml of tetrahydrofuran was treated at −78° under argon with 100 ml of n-butyllithium (1.6M in hexane). The mixture was stirred at −78° for 10 minutes and then a solution of 9.8 g (80 mmol) of 4-hydroxybenzaldehyde in 50 ml of tetrahydrofuran was added within 30 minutes. The reaction mixture was stirred at −78° for a further 20 minutes, then brought to room temperature and treated with 200 ml of saturated ammonium chloride solution. The aqueous phase was extracted twice with ether. The combined organic phases were dried in sequence with saturated sodium sulphate and concentrated The residue was purified by flash chromatography on 1000 g of silica gel (elution agent methylene chloride/ethyl acetate 9:1). There was obtained methyl 4-hydroxy-4-(4-hydroxyphenyl)-2-butynoate as a red oil.

MS: 206 (M+) m/e (b) A solution of 6.2 g (30 mmol) of methyl 4-hydroxy-4-(4-hydroxyphenyl)-2-butynoate in 200 ml of methylene chloride and 50 ml of tetrahydrofuran was added dropwise at 0° to a suspension of 78.4 g (0.9 mol) of manganese dioxide in 200 ml of methylene chloride. The reaction mixture was stirred at room temperature for 20 hours, filtered over magnesium sulphate and concentrated. Purification of the residue by flash chromatography on 600 g of silica gel (elution agent methylene chloride/ethyl acetate 9:1) and subsequent crystallization from ether/hexane yielded methyl 3-(4-hydroxybenzoyl) propiolate of melting point 84°–86°.

EXAMPLE 29

(a) A solution of 8.36 ml (0.1 mol) of methyl propiolate in 100 ml of tetrahydrofuran was treated at −78° under argon with 68.8 ml of n-butyllithium (1.6M in hexane). The mixture was stirred at −78° for 10 minutes and then a solution of 16.6 g (0.1 mol) of 2.5-dimethoxybenzaldehyde in 120 ml of tetrahydrofuran was added within 40 minutes. The reaction mixture was stirred at −78° for a further 20 minutes, then brought to room temperature and treated with 150 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 1000 g of silica gel (elution agent methylene chloride/ethyl acetate 9:1). There was obtained methyl 4-(2.5-dimethoxyphenyl)-4-hydroxy-2-butynoate as a yellow oil.

MS: 250 (M+) m/e (b) A solution of 13.8 g (55 mm ol) of methyl 4-(2,5-dimethoxyphenyl)-4-hydroxy-2-butynoate in 80 ml of methylene chloride is added dropwise at 0° to a suspension of 139 g (1.6 mol) of manganese dioxide in 350 ml of methylene chloride The reaction mixture was stirred at 0° for 1 hour, filtered over magnesium sulphate and concentrated. Crystallization of the residue from methylene chloride/ether yielded methyl 3-(2,5-dimethoxybenzoyl)propiolate of melting point 70°–71°.

EXAMPLE 30

A solution of 2.7 g (9.7 mmol) of methyl 3-(2,3,4-trimethoxybenzoyl)propiolate in 30 ml of tetrahydrofuran was treated slowly at 0° with 27 ml of 3% potassium hydroxide solution and subsequently stirred at 0° for a further 1.5 hours. The reaction mixture was treated with water and extracted once with ether. The ether phase was discarded. The aqueous phase was adjusted to pH 1 with 1N hydrochloric acid and extracted twice with ether. The combined organic phases were dried over sodium sulphate and concentrated. Crystallization of the residue from ethyl acetate/hexane yielded 3-(2,3,4-trimethoxybenzoyl)-propiolic acid of melting point 119°–121°.

EXAMPLE 31

A solution of 2.8 g (10 mmol) of methyl 3-(3,4,5-trimethoxybenzoyl)propiolate in 30 ml of tetrahydrofuran was treated slowly at 0° with 28 ml of 3% potassium hydroxide solution and subsequently stirred at 0° for a further 1.5 hours. The reaction mixture was treated with water and extracted once with ether. The ether phase was discarded. The aqueous phase was adjusted to pH 1 with 1N hydrochloric acid and extracted twice with ether. The combined organic phases were dried over sodium sulphate and evaporated. Crystallization of the residue from methylene chloride/ether/hexane yielded 3-(3,4,5-trimethoxybenzoyl)-propiolic acid of melting point 130°–132°.

EXAMPLE 32

A solution of 5.9 g (25.4 mmol) of methyl 3-[3,4-(methylenedioxy)benzoyl]propiolate in 60 ml of tetrahydrofuran was treated slowly at 0° with 71 ml of 3% potassium hydroxide solution and stirred at 0° for a further 1 hour The reaction mixture was treated with water and extracted once with ether. The ether phase is discarded. The aqueous phase was adjusted to pH 1 with 1N hydrochloric acid and extracted twice with ether. The combined organic phases were dried over sodium sulphate and concentrated. Crystallization of the residue from methylene chloride/ether/hexane yielded 3-[3,4-(methylenedioxy)-benzoyl]propiolic acid of melting point 122°–124°.

EXAMPLE 33

A solution of 6.2 g (28 mmol) of methyl 3-(4-methoxybenzoyl)propiolate in 60 ml of tetrahydrofuran was treated slowly at 0° with 80 ml of 3% potassium hydroxide solution and stirred at 0° for a further 1 hour. The reaction mixture was treated with water and extracted once with ether. The ether phase was discarded. The aqueous phase was adjusted to pH 1 with 1N hydrochloric acid and extracted twice with ether. The combined organic phases were dried over sodium sulphate and concentrated. Precipitation of the residue from methylene chloride/ether/hexane yielded 3-(4-methoxybenzoyl)propiolic acid as an amorphous powder.

MS: 204 (M+) m/e
IR (KBr): 1714, 1641, 1588, 1510, 1262 cm$^{-1}$

EXAMPLE 34

A solution of 5 g (20 mmol) of methyl 3-(2,5-dimethoxybenzoyl)propiolate in 50 ml of tetrahydrofuran was treated slowly at 0° with 56 ml of 3% potassium hydroxide solution and stirred at 0° for a further 1 hour. The reaction mixture was treated with water and extracted once with ether. The ether phase was discarded. The aqueous phase was adjusted to pH 1 with 1N hydrochloric acid and extracted twice with ether. The combined organic phases were dried over sodium sulphate and concentrated. Crystallization of the residue from ether/hexane yielded 3-(2,5-dimethoxybenzoyl)propiolic acid of melting point 91°–93°.

EXAMPLE 35

(a) 41.5 g (0.3 mol) of potassium carbonate were added at 0° to a solution of 18.4 ml (0.3 mol) of propiolic acid in 300 ml of acetone. The mixture was stirred at room temperature for 4 hours, then 34.7 ml (0.3 mol) of 3,3-dimethylallyl bromide were added and the mixture was subsequently boiled at reflux for a further 20 hours. The cooled reaction mixture was concentrated on a rotary evaporator. The residue was poured onto ice/water and extracted twice with ethyl acetate. The combined organic phases were dried over sodium sulphate and concentrated. Distillation of the residue in a water-jet vacuum yielded 3-methyl-2-butenyl propiolate of boiling point 77°–78°/15 mmHg.

MS: 138 (M+) m/e (b) A solution of 6.6 g (4g mmol) of 3-methyl-2-butenyl propiolate in 60 ml of tetrahydrofuran was treated at −78° under argon with 30 ml of n-butyllithium (1.6M in hexane). The mixture was stirred at −78° for 10 minutes and then a solution of 9.4 g (48 mmol) of 3,4,5-trimethoxybenzaldehyde in 80 ml of tetrahydrofuran was added within 30 minutes. The reaction mixture was stirred at −78° for a further 1 hour, then brought to room temperature and treated with 120 ml of saturated ammonium chloride solution The aqueous phase was extracted twice with ether. The organic phases were washed in succession with saturated sodium chloride solution and with water dried over sodium sulphate and concentrated. The residue was purified by flash chromatography on 700 g of silica gel (elution agent methylene chloride/ethyl acetate 9:1). There was obtained 3-methyl-2-butenyl 4-hydroxy-4-(3,4,5-trimethoxyphenyl)-2- butynoate as a yellow oil.

MS: 334 (M+) m/e (c) A solution of 10.7 g (32 mmol) of 3-methyl-2-butenyl 4-hydroxy-4-(3,4,5-trimethoxyphenyl)-2-butynoate in 200 ml of methylene chloride was added dropwise at 0° to a suspension of 84 g (0.97 mol) of manganese dioxide in 200 ml of methylene chloride. The reaction mixture was stirred at 0° for 2 hours, filtered over magnesium sulphate and concentrated. The residue was purified by flash chromatography on 500 g of silica gel (elution agent methylene chloride/ ethyl acetate 9:1) and crystallized from ether/hexane. There was obtained 3-methyl-2-butenyl 3-(3,4,5-trimethoxybenzoyl)propiolate of melting point 52°–53°.

EXAMPLE 36

(a) A solution of 10 g (72 mmol) of 3-methyl-2-butenyl propiolate in 100 ml of tetrahydrofuran was treated at −78° under argon with 47 ml of n-butyllithium (1.6M in hexane). The mixture was stirred at −78° for 10 minutes and then a solution of 10.9 g (72 mmol) of 3,4-methylenedioxybenzaldehyde in 120 ml of tetrahydrofuran was added within 30 minutes. The reaction mixture was stirred at −78° for a further 30 minutes then brought to room temperature and treated with 120 ml of saturated ammonium chloride solution. The aqeuous phase was extracted twice with ether; the organic phases were washed in succession with saturated sodium chloride solution and with water, dried over sodium sulphate and concentrated. The residue was purified by flash chromatography on 1000 g of silica gel (elution agent methylene chloride/ethyl acetate 9:1). There was obtained 3-methyl-2-butenyl 4-hydroxy-4-[3,4-(methylenedioxy)phenyl]-2-butynoate as a yellow oil.

MS: 288 (M+) m/e (b) A solution of 17.2 g (60 mmol) of 3-methyl-2-butenyl 4-hydroxy-4-[3,4-(methylenedioxy)phenyl]-2-butynoate in 250 ml of methylene chloride was added dropwise at 0° to a suspension of 156 g (1.8 mol) of manganese dioxide in 300 ml of methylene chloride. The reaction mixture was stirred at 0° for 1 hour, filtered over magnesium sulphate and concentrated. The residue was purified by flash chromatography on 1000 g of silica gel (elution agent methylene chloride/ether 4:1) and crystallized from ether/hexane. There was obtained 3-methyl-2-butenyl 3-[3,4-(methylene-dioxy)benzoyl]propiolate of melting point 52°–53°.

EXAMPLE 37

(a) A solution of 10 g (72 mmol) of 3-methyl-2-butenyl propiolate in 100 ml of tetrahydrofuran was treated at −78° under argon with 47 ml of n-butyllithium (1.6M in hexane). The mixture was stirred at −78° for 10 minutes and then a solution of 8.8 ml (72 mmol) of 4-methoxybenzaldehyde in 100 ml of tetrahydrofuran was added within 30 minutes. The reaction mixture was stirred at −78° for a further 30 minutes, then brought to room temperature and treated with 100 ml of saturated ammonium chloride solution. The aqueous phase was extracted twice with ether. The organic phases were washed in succession with saturated sodium chloride solution and with water, dried over sodium sulphate and concentrated. The residue was purified by flash chromatography on 1000 g of silica gel (elution agent methylene chloride/ethyl acetate 9:1). There was obtained 3-methyl-2-butenyl 4-hydroxy-4-(4-methoxyphenyl)-2-butynoate as a yellow oil.

MS: 274 (M+) m/e (b) A solution of 10.7 g (39 mmol) of 3-methyl-2-butenyl 4-hydroxy-4-(4-methoxyphenyl)-2-butynoate in 150 ml of methylene chloride was added dropwise at 0° to a suspension of 101.7 g (1.17 mol) of manganese dioxide in 200 ml of methylene chloride. The reaction mixture was stirred at 0° for 1 hour, filtered over magnesium sulphate and concentrated. The residue was purified by flash chromatography on 700 g of silica gel (elution agent methylene chloride/ ether 4:1). There was obtained 3-methyl-2-butenyl 3-(4-methoxybenzoyl)propiolate as a yellow oil.

MS: 272 (M+) m/e
IR (film): 1717, 1646, 1596, 1260, 1231, 1166 cm$^{-1}$

EXAMPLE 38

(a) 12.3 ml (0.2 mol) of propiolic acid were boiled at reflux for 20 hours together with 23.6 ml (0.2 mol) of diethylene glycol monomethyl ether, 1.5 g (8 mmol) of P-toluenesulphonic acid monohydrate and 80 ml of toluene, with the resulting reaction water being distilled off azeotropically and being collected in a water separator. After completion of the water separation the reaction mixture was washed in succession with saturated sodium bicarbonate solution and with water. The toluene phase was dried over sodium sulphate and concentrated. The crude product was purified by flash chromatography on 500 g of silica gel (elution agent methylene chloride/ethyl acetate 9:1). There was obtained 2-(2-methoxyethoxy)ethyl propiolate as a colorless oil.

(b) A solution of 10 g (58 mmol) of 2-(2-methoxyethoxy)-ethyl propiolate in 80 ml of tetrahydrofuran is treated at −78° under argon with 36 ml of n-butyllithium (1.6M in hexane). The mixture was stirred at −78° for 10 minutes and then a solution of 7 ml (58 mmol) of 4-methoxybenzaldehyde in 60 ml of tetrahydrofuran was added within 30 minutes. The reaction mixture was stirred at −78° for a further 30 minutes, then brought to room temperature and treated with 150 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 500 g of silica gel (elution agent methylene chloride/ether 4:1). There was obtained 2-(2-methoxyethoxy)ethyl 4-hydroxy-4-(4-methoxyphenyl)-2-butynoate as a red oil.

MS: 291 (M-OH) m/e (c) A solution of 9.8 g (32 mmol) of 2-(2-methoxyethoxy)-ethyl 4-hydroxy-4-(4-methoxyphenyl)-2-butynoate in 100 ml of methylene chloride was added dropwise at 0° to a suspension of 83 g (0.95 mol) of manganese dioxide in 150 ml of methylene chloride. The reaction mixture was stirred at 0° for 2 hours, filtered over magnesium sulphate and concentrated. The residue was purified by flash chromatography on 800 g of silica gel (elution agent methylene chloride/ether 4:1). There was obtained 2-(2-methoxyethoxy)ethyl 3-(4-methoxybenzoyl)propiolate as a pale yellow oil.

MS: 248 (M-CH$_2$=CH−OCH$_3$) m/e
IR (film): 1720, 1646, 1596, 1261 cm$^{-1}$

EXAMPLE 39

(a) A solution of 10 g (58 mmol) of 2-(2-methoxyethoxy)ethyl propiolate in 80 ml of tetrahydrofuran was treated at −78° under argon with 36 ml of n-butyllithium (1.6M in hexane). The mixture was stirred at −78° for 10 minutes and then a solution of 11.4 g (58 mmol) of 3,4,5-trimethoxy-benzaldehyde in 60 ml of tetrahydrofuran was added within 30 minutes. The reaction mixture was stirred at −78° for a further 30 minutes, then brought to room temperature and treated with 150 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 1000 g of silica gel (elution agent methylene chloride/ether 4:1). There was obtained 2-(2-methoxyethoxy)ethyl 4-hydroxy-4-(3,4,5-trimethoxyphenyl)-2-butynoate as a red oil.

MS: 368 (M+) m/e (b) A solution of 8.5 g (23 mmol) of 2-(2-methoxyethoxy)-ethyl 4-hydroxy-4-(3,4,5-trimethoxyphenyl)-2-butynoate in 100 ml of methylene chloride was added dropwise at 0° to a suspension of 60 g (0.69 mol) of manganese dioxide in 150 ml of methylene chloride. The reaction mixture was stirred at 0° for 2 hours, filtered over magnesium sulphate and concentrated. The residue was purified by flash chromatography on 700 g of silica gel (elution agent methylene chloride/ether 4:1) and subsequently crystallized from ether/hexane. There was obtained 2-(2-methoxyethoxy)ethyl 3-(3,4,5-trimethoxybenzoyl)propiolate of melting point 33°–34°.

EXAMPLE 40

(a) A solution of 6.9 g (40 mmol) of 2-(2-methoxyethoxy)-ethyl propiolate in 60 ml of tetrahydrofuran was treated at −78° under argon with 25 ml of n-butyllithium (1.6M in hexane). The mixture was stirred at −78° for 10 minutes and then a solution of 6 g (40 mmol) of 3,4-methylenedioxy-benzaldehyde in 60 ml of tetrahydrofuran was added within 30 minutes. The reaction mixture was stirred at −78° for a further 30 minutes then brought to room temperature and treated with 100 ml of saturated ammonium chloride solution The aqueous phase was extracted twice with ether. The combined organic phases were washed in succession with saturated sodium chloride solution and with water, dried over sodium sulphate and concentrated. The residue was purified by flash chromatography on 600 g of silica gel (elution agent methylene chloride/ether 4:1). There was obtained 2-(2-methoxyethoxy)ethyl 4-hydroxy-4-[3,4(methylenedioxy)phenyl]-2-butynoate as a yellow oil.

MS: 322 (M+) m/e (b) A solution of 7.9 g (24.5 mmol) of 2-(2-methoxyethoxy)ethyl 4-hydroxy-4-[3,4-(methylenedioxy)-phenyl]-2butynoate in 100 ml of methylene chloride was added dropwise at 0° to a suspension of 64 g (0.74 mol) of manganese dioxide in 150 ml of methylene chloride. The reaction mixture was stirred at 0° for 2 hours, filtered over magnesium sulphate and concentrated. The residue was purified by flash chromatography on 800 g of silica gel (elution agent methylene chloride/ether 4:1). There was obtained 2-(2-methoxyethoxy)ethyl 3-[3,4-(methylenedioxy)-benzoyl]propiolate as a yellow oil.

MS: 320 (M+) m/e
IR (film): 1719, 1643. 1601. 1445, 1261 cm$^{-1}$

EXAMPLE 41

0.815 g of acetyl chloride and 0.827 g of pyridine were added simultaneously to a solution of 2.0 g (7.99 mmol) of 4-hydroxy-1-(3,4,5-trimethoxyphenyl)-2-butyn-1-one in 20 ml of methylene chloride. The reaction mixture was stirred at 0° for 1 hour, whereupon it was treated with 30 ml of phosphate buffer (pH 6) and the aqueous phase was extracted twice with methylene chloride. The combined organic phases were dried over magnesium sulphate and evaporated. The residue was recrystallized from ethyl acetate/hexane and there was obtained 3-(3,4,5-trimethoxy-benzoyl)-2-propynyl acetate of melting point 104°–105°.

EXAMPLE 42

2.21 g (9.59 mmol) of 3,4,5-trimethoxybenzoyl chloride in 10 ml of methylene chloride and 1 ml of pyridine were o added simultaneously at 0° to a solution of 2.0 g (7.99 mmol) of 4-hydroxy-1-(3,4,5-trimethoxyphenyl)-2-butyn-1-one in 25 ml of methylene chloride. The reaction mixture was stirred at 0° for 30 minutes and at room temperature for 1.5 hours, Whereupon 30 ml of 0.5M hydrochloric acid and 100 ml of methylene chloride were added and the aqueous phase was extracted twice with methylene chloride. The combined organic phases were dried over magnesium sulphate and evaporated, and the residue was chromatographed on silica gel with ether. After recrystallization from ethyl acetate/hexane there was obtained 3-(3,4,5-trimethoxybenzoyl)-2-propynyl 3,4,5-trimethoxybenzoate of melting point 106°–108°.

EXAMPLE 43

43.6 ml of n-butyllithium solution (1.6M in hexane) are added at −78° to a solution of 10 ml (69.8 mmol) of 3,3-diethoxy-1-propyne in 210 ml of absolute tetrahydrofuran. The mixture was stirred at −78° for 30 minutes and treated at −40° with 13.70 g (69.8 mmol) of 3,4,5-trimethoxybenzaldehyde in 60 ml of tetrahydrofuran. The reaction mixture was stirred at 0° for 1 hour and treated with 100 ml of saturated ammonium chloride solution and 150 ml of ether. The aqueous phase was extracted twice with ether. The combined organic phases were dried over magnesium sulphate and evaporated. The residue was dissolved in 100 ml of methylene chloride and added dropwise at 0° to a suspension of 176.8 g of manganese dioxide in 300 ml of methylene chloride. The reaction mixture was stirred at 0° for 20 minutes, filtered over magnesium sulphate and evaporated. The residue was crystallized from iso-octane at 0° and there is obtained 4,4-diethoxy-1-(3,4,5-trimethoxyphenyl)-2-butyn-1-one of melting point 52°–54°.

EXAMPLE 44

3 ml of 60% perchloric acid were added at room temperature to a solution of 2.0 g (6.2 mmol) of 4,4-diethoxy-1-(3,4,5-trimethoxyphenyl)-2-butyn-1-one in 10 ml of dioxan. The reaction mixture was stirred at room temperature for 2 hours and treated with 20 ml of ether and 10 ml of water. The aqueous phase was extracted three times with ether. The combined ether phases were dried over magnesium sulphate and evaporated. Chromatography of the residue on silica gel yielded, in addition to unreacted starting material. 3-(3,4,5-trimethoxybenzoyl)-2-propynal of melting point 86° (dec.).

MS: 248 (M+) m/e

EXAMPLE 45

A solution prepared at −40° from 0.66 g (9.40 mmol) of 3-butyn-2-ol, 12.55 ml of n-butyllithium solution (1.6M in hexane) and 6 ml of hexamethylphosphortriamide in 20 ml of absolute tetrahydrofuran was added dropwise at −40° to a solution of 2.0 g (7.83 mmol) of N,3,4,5-tetramethoxy-N-methylbenzoylamide in 20 ml of absolute tetrahydrofuran. The reaction mixture was stirred at −40° for 15 minutes, warmed slowly to 0° and stirred at 0° for 1 hour and at room temperature for 1 hour, whereupon 20 ml of 5% ethanolic hydrochloric acid and 100 ml of ether were added. The organic phase was washed three times with water, dried over magnesium sulphate and evaporated. After chromatography of the residue on silica gel with ether and crystallization from ethyl acetate/hexane there was obtained 4-hydroxy-1-(3,4,5-trimethoxyphenyl)-2-pentyn-1-one of melting point 77°–79°.

EXAMPLE 46

(a) 72 ml of n-butyllithium solution (1.6M in hexane) were added at −110° to a solution of 11.72 ml (0.115 mol) of ethyl propiolate in 195 ml of tetrahydrofuran/ether/hexane (4:2:1). The mixture was stirred at −110° for 20 minutes and then treated with 15.0 g (76.4 mmol) of 3,4,5-trimethoxybenzaldehyde in 30 ml of tetrahydrofuran. The mixture was thereafter stirred at −78° for 1.5 hours and treated at −30° with 100 ml of saturated ammonium chloride solution and 100 ml of ethyl acetate. The aqueous phase was extracted twice with ethyl acetate. The combined organic phases were dried over magnesium sulphate and evaporated. The residue was chromatographed on 500 g of silica gel with ethyl acetate/hexane (1:1), whereafter there was obtained ethyl 4-hydroxy-4-(3,4,5-trimethoxyphenyl)-2-butynoate.

IR (film): 2220(w), 1712(s), 1595(s), 1244(s), 1127(s).

(b) A solution of 21.6 g (73.4 mmol) of ethyl 4-hydroxy-4-(3,4,5-trimethoxyphenyl)-2-butynoate in 80 ml of methylene chloride was added dropwise at 0° to a suspension of 191.4 g (2.2 mol) of manganese dioxide in 330 ml of methylene chloride. The reaction mixture was stirred at 0° for 30 minutes filtered over magnesium sulphate and evaporated. The residue was crystallized from ethyl acetate/hexane at 0° overnight. There was obtained ethyl 3-(3,4,5-trimethoxybenzoyl)-2-propiolate of melting point 61°–62.5°.

EXAMPLE 47

8.7 ml of n-butyllithium solution (1.6M in hexane) were added at −78° to a solution of 3.0 g (13.5 mmol) of 1-(3,4,5-trimethoxyphenyl)-2-propyn-1-ol in 40 ml of ether. The reaction mixture was brought to −30°, whereupon 1.8 ml (14.2 mmol) of freshly distilled trimethylsilyl chloride were added at −30°. Thereafter, the mixture was warmed to 0°, stirred and cooled to −78° for 1 hour, whereupon 7.8 ml of n-butyllithium solution (1.6M in hexane) were added. The reaction mixture was stirred at −30° for 1 hour and then treated at −30° with 2.77 ml (20.25 mmol) of butyl chloroformate, whereupon the mixture was stirred at −30° for 30 minutes and at 0° for 1 hour and 150 ml of 1N hydrochloric acid and 150 ml of ethyl acetate were added. Subsequently, 30 ml of 25% hydrochloric acid were added, the mixture was shaken vigorously for 10 minutes in a separating funnel, the aqueous phase was extracted twice with ethyl acetate, the combined organic phases were dried over magnesium sulphate and the solvent was distilled off. The crude product which remained behind as the residue was taken up in 10 ml of methylene chloride and added dropwise at 0° to a suspension 35.2 g (0.405 mol) of manganese dioxide in 50 ml of methylene chloride. The reaction mixture was stirred at 0° for 1.5 hours, filtered over magnesium sulphate and evaporated. After chromatography of the residue on silica gel with ethyl acetate/hexane (1:4) there was obtained butyl 3-(3,4,5-trimethoxybenzoyl)-propiolate as a pale yellowish oil.

IR (film): 1719(s), 1647(m), 1582(m), 1501(m), 1415(m). 1334(s), 1248(s), 1128(s).

EXAMPLE 48

(a) A solution of 9.76 g (64.78 mmol) of tert.-butyldimethylsilyl chloride in 50 ml of methylene chloride was added dropwise at 0° to a solution of 12.0 g (53.98 mmol) of α-ethynyl-3,4,5-trimethoxybenzyl alcohol in 100 ml of methylene chloride and 9.65 ml of 1,8-diazabicyclo[5.4.0]-undec-7-ene. The reaction mixture was stirred at 0° for 30 minutes and at room temperature for 1 hour, whereupon 100 ml of phosphate buffer (pH 6) were added. The aqueous phase was extracted twice with 50 ml of ether, and the combined organic phases were dried over magnesium sulphate and evaporated. The residue was chromatographed on 500 g of silica gel with ether/petroleum ether (4:1), whereafter 1-[(tert-)butyldimethylsiloxy]-1-(3,4,5-trimethoxyphenyl)-2-propyne was obtained.

IR (film): 3282(w), 2955(s), 2932(s), 1594(s), 1506(m), 1463(s), 1417(m), 1332(m), 1097(s), 837(s).

(b) 5.6 ml of n-butyllithium solution (1.6M in hexane) were added at −78° to a solution of 3.0 g (8.9 mmol) of 1-[(tert)butyldimethylsiloxy]-1-(3,4,5-trimethoxyphenyl)-2-propyne in 25 ml of absolute tetrahydrofuran. The reaction mixture was brought slowly to 0° and stirred at 0° for a further 15 minutes, whereupon 1.1 ml of N,N-dimethylcarbamoyl chloride was added at −78°. The reaction mixture was stirred at −78° for 30 minutes and at 0° for 2 hours, treated with 10 ml of 2N hydrochloric acid and 10 ml of dioxan and stirred at room temperature for 12 hours. After the addition of 50 ml of ether and 50 ml of water the organic phase was dried over magnesium sulphate and evaporated. The residue was chromatographed on silica gel with ethyl acetate, whereafter there was obtained a pale yellow viscous oil which was taken up in 5 of methylene chloride and added at 0° to a suspension of 10.2 g of manganese dioxide in 15 ml of methylene chloride. The reaction mixture was stirred at 0° for 2.5 hours, filtered over magnesium sulphate and evaporated. The residue was crystallized from ethyl acetate/hexane at 0°, whereby there was obtained N,N-dimethyl-3-(3,4,5-trimethoxybenzoyl)propiolamide of melting point 118°-119°.

EXAMPLE 49

(a) A solution of 11.7 g (50 mmol) of triethyl 3-trimethylsilylorthopropiolate (see G. Roche & J. Bigalke, Tetrahedron Letters 1984, 955) in 100 ml of dry tetrahydrofuran was treated dropwise at −5° to 0° with 31.25 ml of 1.6M butyllithium solution in hexane. After completion of the addition the mixture was stirred at −10° for 1 hour, then treated with a further 3.0 ml of 1.6M butyllithium solution in hexane and stirred at 0° for a further 10 minutes. Thereupon, a solution of 9.81 g (50 mmol) of 3,4,5-trimethoxybenzaldehyde in 60 ml of tetrahydrofuran was added dropwise at −5°. The reaction mixture was held at 10° for 10 minutes and subsequently allowed to warm to room temperature within one hour. For the working-up, the mixture was treated with saturated NaHCO$_3$ solution, diluted with ether/hexane 1:1. the phases were separated and the aqueous phase was extracted with hexane/ether. The combined organic phases were washed with water, saturated sodium bicarbonate solution and sodium chloride solution, dried over sodium sulphate, filtered and evaporated. Chromatography on silica gel with hexane/ethyl acetate 30%→50%/triethylamine 0.1% yielded 4-hydroxy-4-(3,4,5- trimethoxyphenyl)-2-butyne ortho acid triethyl ester as a yellow oil.

IR (film): 3465 (br, OH); 2230 (C≡C).

NMR (250 MHz. CDCl$_3$): 6.79 (s, 2 aromatic H); 5.48 (d, J=6.5, H-C(4)); 3.87 (s, 2 OCH$_3$); 3.85 (s, 1 OCH$_3$); 3.71 (q, J=7, 3 OCH$_2$CH$_3$); 2.37 (d, J=6.5, OH); 1.24 (t. J=7, 3 OCH$_2$CH$_3$).

MS: 368 (44, M+); 323 (88, M+-OEt); 197 (63); 169 (100).

(b) A solution of 8.49 g (23 mmol) of 4-hydroxy-4-(3,4,5-trimethoxyphenyl)-2-butyne ortho acid triethyl ester in 100 ml of dichloromethane was treated with 10.0 g of manganese dioxide, whereupon the suspension was stirred at room temperature for 3.5 hours. Thereafter, the mixture was filtered over a bed of Hyflo, the filtrate was evaporated and the residue was chromatographed on silica gel with hexane/ethyl acetate 12%→20%/triethylamine 0.1%. There was thus obtained 4-oxo-4-(3,4,5-trimethoxyphenyl)-2-butyne ortho acid triethyl ester as a yellowish, viscous oil which solidified upon storage at −15°. A sample for analysis was obtained by crystallization from pentane at −15°; m.p. 29°-31°.

IR (film): 2220 (C≡C); 1647 (C=O conj.).

NMR (250 MHz, CDCl$_3$): 7.42 (s, 2 aromatic, H); 3.95 (s, 1 OCH$_3$); 3.92 (s, 2 OCH$_3$); 3.79 (q, J=7, 3 OCH$_2$CH$_3$); 1.28 (t, J=7, 3 OCH$_2$CH$_3$).

MS: 366 (44, M+); 321 (100, M+-OEt); 195 (64); 147 (42, (EtO)$_3$C+).

Anal. calc. for C$_{19}$H$_{26}$O$_7$ (366.41); C 62.28. H 7.15; found C 61.96, H 7.29.

EXAMPLE 50

(a) A solution of 29.6 ml (0.5 mol) of 2-propyn-1-ol in 500 ml of tetrahydrofuran was treated at −78° under argon with 67.3 g (0.6 mol) of potassium tert.-butylate. The mixture was stirred at −78° for 4 hours. 69.4 ml (0.6 mol) of 3,3-dimethylallyl bromide were then added and the mixture was stirred at −78° for a further 3 hours and at at room temperature for 20 hours. The reaction mixture was poured on to ice/water and extracted twice with ether. The combined organic phases were dried over magnesium sulphate and concentrated. There was obtained 1-[(3-methyl-2-butenyl)oxy]-2-propyne as a yellow oil which was processed without purification.

MS: 123 (M-H), 109 (M-CH$_3$) m/e.

(b) A solution of 15 g (121 mmol) of 1-[(3-methyl-2-butenyl)oxy]-2-propene in 150 ml of tetrahydrofuran was treated at −78° under argon with 83 ml of n-butyllithium (1.6M in hexane). The mixture was left to stir at −40° for 30 minutes, again cooled to −78° and a solution of 26.1 g (133 mmol) of 3,4,5-trimethoxybenzaldehyde in 150 ml of tetrahydrofuran was then added within 40 minutes. The reaction mixture was stirred at −78° for a further 1 hour, then warmed to room temperature and subsequently treated with 150 ml of saturated ammonium chloride solution. The aqueous phase was extracted twice with ether. The combined organic phases were washed in succession with saturated sodium chloride solution and with water, dried over magnesium sulphate and concentrated. The residue was purified by flash chromatography on 1000 g of silica gel (elution agent methylene chloride/ether 4:1). There was obtained 1-hydroxy-4-[(3-methyl-2-butenyl)oxy]-3,4,5-trimethoxyphenyl)-2-butyne as a yellow oil.

MS: 320 (M+), 197 (base peak) m/e.

IR (film): 3124, 1594, 1505, 1324, 1127 cm$^{-1}$.

(c) A solution of 30 g (93.6 mmol) of 1-hydroxy-4-[(3-methyl-2-butenyl)oxy]-1-(3,4,5-trimethoxyphenyl)-2-butyne in 350 ml of methylene chloride was added dropwise at 0° to a suspension of 122 g (1.4 mol) of manganese dioxide in 500 ml of methylene chloride. The reaction mixture was stirred at 0° for 3 hours, filtered over magnesium sulphate and concentrated. Flash chromatography of the residue on 1000 g of silica gel (elution agent methylene chloride/ethyl acetate 9:1) and subsequent crystallization of the product from ether/hexane yielded 4-[(3-methyl-2-butenyl)oxy]-1-(3,4,5-trimethoxyphenyl)-2-butyn-1-one of melting point 32°.

EXAMPLE 51

(a) A solution of 20 g (161 mmol) of 1-[(3-methyl-2-butenyl)oxy)-2-propyne in 200 ml of tetrahydrofuran was treated at −78° under argon with 111 ml of n-butyllithium (1.6M in hexane). The mixture was left to stir at −40° for 30 minutes, again cooled to −78° and a solution of 26.6 g (177 mmol) of 3,4-methylenedioxybenzaldehyde in 150 ml of tetrahydrofuran was then added within 40 minutes. The reaction mixture was stirred at −78° for a further 1 hour, then warmed to room temperature and subsequently treated with 150 ml of saturated ammonium chloride solution. The aqueous phase was extracted twice with ether. The combined organic phases were washed in succession with saturated sodium chloride solution and with water, dried over magnesium sulphate and concentrated. The residue was purified by flash chromatography on 1000 g of silica gel (elution agent methylene chloride/ethyl acetate 9:1). There was obtained 1-hydroxy-4-[(3-methyl-2-butenyl)oxy]-1-[3,4-(methylenedioxy)phenyl]-2-butyne as a yellow oil.

MS: 274 (M+) 243. 149, 131 m/e.

IR (film): 3393, 1486, 1443, 1246, 1039 cm$^{-1}$.

(b) A solution of 34.2 g (125 mmol) of 1-hydroxy-4-[(3-methyl-2-butenyl)oxy)-1-(3,4-(methylenedioxy)phenyl]-2-butyne in 350 ml of methylene chloride was added dropwise at 0° to a suspension of 163 g (1.87 mol) of manganese dioxide in 500 ml of methylene chloride. The reaction mixture was stirred at 0° for 2 hours, filtered over magnesium sulphate and concentrated. The crude product was recrystallized from ether/hexane at −50°. There was obtained 4-[(3-methyl-2-butenyl)oxy]-1-[3,4-(methylenedioxy)phenyl]-2-butyn-1-one as pale yellow crystals which melt at room temperature.

MS: 272 (M+), 149 (base peak) m/e.
IR (film): 2230, 1640, 1602, 1444, 1262 cm$^{-1}$.

EXAMPLE 52

(a) 64 ml (0.43 mol) of 1,8-diazabicyclo[5.4.0]undec-7-ene were added to a solution of 26.4 ml (0.43 mol) of propiolic acid in 400 ml of methylene chloride at 25°, where required while cooling with ice. The mixture was stirred at 25° for 2 hours, then 56 ml (415 mmol) of 4-methoxybenzyl chloride were added and the mixture was finally stirred at 25° for a further 2 days. The reaction mixture was washed in succession with 200 ml of saturated sodium hydrogen carbonate solution and twice with 200 ml of water each time. The organic phase was dried over sodium sulphate and concentrated. The residue was purified by flash chromatography on 1000 g of silica gel (elution agent hexane/ethyl acetate 9:1). There was obtained 4-methoxybenzyl propiolate as a colorless oil.

MS: 190 (M+), 121 (base peak) m/e.

(b) A solution 46.7 g (245.5 mmol) of 4-methoxybenzyl propiolate in 600 ml of tetrahydrofuran was treated at −78° under argon within 1.5 hours with 169 ml of n-butyllithium (1.6M in hexane). The mixture was stirred for 10 minutes and a solution of 36.8 g (245.5 mmol) of 3,4-methylene-dioxybenzaldehyde in 200 ml of tetrahydrofuran was then added within 1 hour. The reaction mixture was stirred at −78° for a further 15 minutes and then poured into a mixture of 300 g of ice and 300 ml of saturated ammonium chloride solution. The aqueous phase was extracted twice with ether. The organic phases were washed in succession with saturated sodium chloride solution and with water dried over sodium sulphate and concentrated. The residue was purified by flash chromatography on 3.5 kg of silica gel (elution agent methylene chloride/ethyl acetate 9:1). There was obtained 4-methoxybenzyl 4-hydroxy-4-(3,4-methylenedioxyphenyl)-2-butynoate as a brown oil.

MS: 340 (M+), 121 (base peak) m/e.
IR (film); 3400, 2230, 1710, 1612, 1513, 1249 cm$^{-1}$.

(c) A solution of 53 g (155 mmol) of 4-methoxybenzyl 4-hydroxy-4-(3,4-methylenedioxyphenyl)-2-butynoate in 400 ml of methylene chloride was added dropwise at 0° to a suspension of 338 g (3.9 mol) of manganese dioxide in 800 ml of methylene chloride The reaction mixture was stirred at 0° for 1 hour, treated with 4 spatula tips of sodium sulphate, suction filtered over Dicalit and concentrated. Crystallization of the residue from ether yielded 4-methoxybenzyl 3-[3,4-(methylenedioxy)benzoyl]propiolate of melting point 113°–114°.

EXAMPLE 53

A solution of 36.3 g (107 mmol) of 4-methoxybenzyl 3-[3,4-(methylenedioxy)benzoyl]propiolate in 300 ml of methylene chloride was treated at room temperature with 6.4 ml (215 mmol) of anhydrous trifluoroacetic acid. The reaction mixture was stirred at room temperature until crystallization began, then cooled to 0° and stirred for a further 30 minutes. The separated crystals were filtered off under suction, washed with cold methylene chloride and dried in a high vacuum. There was obtained 3-(3,4-(methylenedioxy)benzoyl]propiolic acid of melting point 137°.

EXAMPLE A

Crystalline compounds of formulae I and II and pharmaceutically usable salts of compounds of formula I can be used as active substances for the manufacture of hard gelatine capsules, the content of which has the following composition per capsule:

| | |
|---|---|
| Active substance | 50–250.0 mg |
| Lactose powd. | 40.0 mg |
| Lactose cryst. | 230–30.0 mg |
| Maize starch white | 20.0 mg |
| Talc | 8.0 mg |
| Magnesium stearate | 2.0 mg |
| Fill weight per capsule | 250.0 mg |

The active substance and the adjuvants are mixed with one another and the mixture is filled into hard gelatine capsules of suitable size. If required the capsules are subsequently provided with a gastric fluid-resistant coating consisting of hydropropylmethylcellulose phthalate.

EXAMPLE B

Non-crystalline compounds of formulae I and II can be used as described hereinafter as active substances for the manufacture of soft gelatine capsules. The abbreviations used have the following meanings:

BHA=Butylated hydroxyanisole
BHT=Butylated hydroxytoluene
PEG=Polyethylene glycol (a) 0.2 mg of BHA and 1.0 mg of ascorbyl palmitate are dissolved in 400 mg of PEG 400 at room temperature under a nitrogen atmosphere. The solution is treated with 50–250 mg of active substance at room temperature. After all has dissolved the mixture obtained is filled in liquid form into soft gelatine capsules.

(b) 300 mg of PEG 400 and 100 mg of PEG 4000 are warmed under nitrogen until the mixture has liquefied. Thereafter, 0.1 mg of BHA, 0.1 mg of BHT and 0.1 mg of ascorbyl palmitate are added thereto under nitrogen. After all has dissolved 50–250 mg of active substance are added under nitrogen and dissolved while mixing thoroughly. The liquid is then filled into soft gelatine capsules.

(c) 0.2 mg of BHA, 0.2 mg of BHT and 1.0 mg of ascorbyl palmitate are dissolved in 400 mg of Polysorbate-80 at room temperature under nitrogen. The mixture is treated with 50–250 mg of active substance under nitrogen. After all has dissolved the liquid is filled into soft gelatine capsules.

(d) A mixture of in each case 200 mg of Polysorbate-60 and polysorbate-80 is warmed. The liquid mixture obtained is treated under nitrogen with 0.2 mg of BHA. 1.0 mg of α-tocopherol and 2.0 mg of ascorbyl palmitate. After all has dissolved 50–250 mg of active substance are added under nitrogen. After mixing thoroughly until solution is complete the mixture obtained is filled into soft gelatine capsules.

We claim:

1. A compound of the formula

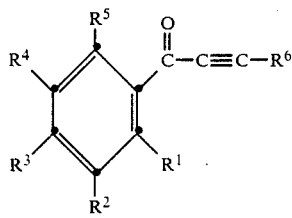

wherein $R^1$, $R^2$, $R^3$, $R^4$ and $R^5$ are independently hydrogen, halogen, lower alkyl, lower alkoxy-lower-alkyl, hydroxy, lower alkoxy, lower alkenyloxy, lower alkynyloxy, lower alkoxy-lower-aloxy, acyloxy, aryl-lower-alkoxy, lower alkylthio, lower alkoxy-lower-alkylthio, lower alkenylthio, lower alkynylthio, aryl-lower-alkylthio, amino which can be monosubstituted by lower alkyl or disubstituted with lower alkyl or lower alkyl and acyl or trifluoromethyl, or two of these substituents which are adjacent jointly and together with the carbon atoms to which they are attached form a 5- to 7-membered ring, and wherein of the substituents $R^1$ to $R^5$ at least two are hydrogen and at least one is different from hydrogen; and $R^6$ is a group of the formula —COOR$^7$,            (a)

—CONR$^8$R$^9$,         (b)

—C(R$^{10}$)=O,         (c)

—C(R$^{11}$)(OR$^{12}$)$_2$, (d)

—C(OR$^{13}$)$_3$          (e)

or

OC(R$^{14}$)(R$^{15}$)OR$^{16}$;  (f)

in which $R^7$ is hydrogen, lower alkyl, lower alkoxy-lower-alkoxy-lower alkyl, aryl-lower alkyl or lower alkenyl, $R^8$ and $R^9$ are lower alkyl, $R^{10}$ is hydrogen, $R^{11}$ is hydrogen, $R^{12}$ is lower alkyl, $R^{13}$ is lower alkyl, $R^{14}$ is hydrogen, $R^{15}$ is hydrogen or lower alkyl and $R^{16}$ is hydrogen, lower alkenyl, lower alkoxy-lower-alkyl or acyl, or a pharmaceutically acceptable salt of an acidic compound of formula with an acid base or of a basic compound of formula with an acid.

2. A compound in accordance with claim 1, wherein $R^1$, $R^2$, $R^3$, $R^4$ and $R^5$ are independently hydrogen, lower alkyl, hydroxy, lower alkoxy, lower alkylthio or di-lower-alkylamino or two of these substituents which are adjacent together are lower alkylene or lower alkylenedioxy, provided that of the substituents $R^1$ to $R^5$ at least one is different from hydrogen and at least two are hydrogen.

3. A compound in accordance with claim 2, wherein $R^1$ is hydrogen.

4. A compound in accordance with claim 3, wherein $R^1$ and $R^2$ are hydrogen and $R^3$, $R^4$ and $R^5$ are lower.

5. A compound in accordance with claim 3, wherein $R^1$ and $R^5$ are hydrogen and $R^2$, $R^3$ and $R^4$ are lower.

6. A compound in accordance with claim 3, wherein $R^1$, $R^3$ and $R^4$ are hydrogen and $R^2$ and $R^5$ are lower.

7. A compound in accordance with claim 3, wherein $R^1$, $R^2$ and $R^5$ are hydrogen and $R^3$ and $R^4$ together are lower alkylenedioxy or lower alkylene.

8. A compound in accordance with claim 3, wherein $R^1$, $R^2$, $R^4$ and $R^5$ are hydrogen and $R^3$ is halogen, lower alkyl, hydroxy, lower alkoxy, lower alkylthio or di-lower.

9. A compound in accordance with claim 1, wherein $R^6$ is a group of formula (a), (b), (c), (d) or (f) and $R^{16}$ is hydrogen, lower alkoxy-lower-alkyl or acyl.

10. A compound in accordance with claim 1, wherein $R^1$ and $R^2$ are hydrogen and $R^3$, $R^4$ and $R^5$ are methoxy or $R^1$ and $R^5$ are hydrogen and $R^2$, $R^3$ and $R^4$ are methoxy and $R^6$ is a group of formula (a), (b) or (f) in which $R^7$ is hydrogen, methyl or methoxyethoxyethyl, $R^8$ and $R^9$ are methyl $R^{14}$ is hydrogen, $R^{15}$ is hydrogen or methyl and $R^{16}$ is hydrogen or 1-ethoxyethyl.

11. A compound according to claim 1, wherein $R^1$ and $R^5$ are hydrogen and $R^2$, $R^3$ and $R^4$ are methoxy and $R^6$ is a group of formula (a), (b) or (f) in which $R^7$ is hydrogen, methyl or methoxyethoxyethyl, $R^8$ and $R^9$ are methyl, $R^{14}$ is hydrogen, $R^{15}$ is hydrogen or methyl and $R^{16}$ is hydrogen or 1-ethoxyethyl.

12. A compound according to claim 1, wherein $R^1$, $R^3$ and $R^4$ are hydrogen and $R^2$ and $R^5$ are methoxy and $R^6$ is a group of formula (a), (b) or (f) in which $R^7$ is hydrogen, methyl or methoxyethoxyethyl, $R^8$ and $R^9$ are methyl, $R^{14}$ is hydrogen, $R^{15}$ is hydrogen or methyl and $R^{16}$ is hydrogen or 1-ethoxyethyl.

13. A compound according to claim 1, wherein $R^1$, $R^2$ and $R^5$ are hydrogen and $R^3$ and $R^4$ together are methylenedioxy and $R^6$ is a group of formula (a), (b) or (f) in which $R^7$ is hydrogen, methyl or methoxyethoxyethyl, $R^8$ and $R^9$ are methyl, is hydrogen, $R^{15}$ is hydrogen or methyl and $R^{16}$ is hydrogen or 1-ethoxyethyl.

14. A compound according to claim 1, wherein $R^1$, $R^2$, $R^4$ and $R^5$ are hydrogen and $R^3$ is chlorine, fluorine, methyl, hydroxy, methoxy or methylthio and $R^6$ is a group of formula (a), (b) or (f) in which $R^7$ is hydrogen, methyl or methoxyethoxyethyl, $R^8$ and $R^9$ are methyl, $R^{14}$ is hydrogen, $R^{15}$ is hydrogen or methyl and $R^{16}$ is hydrogen or 1-ethoxyethyl.

15. A compound according to claim 1 which is 3-[3,4-(methylenedioxy)benzoyl]propiolic acid.

16. A compound according to claim 1 which is 4-hydroxy-1-(3,4,5-trimethoxyphenyl)-2-butyn-1-one.

17. A compound according to claim 1 which is 3-(4-methoxybenzoyl)propiolic acid.

18. A compound according to claim 1 which is methyl 3-(2,3,4-trimethoxybenzoyl)propiolate.

19. A compound according to claim 1 which is methyl 3-(4-hydroxybenzoyl)propiolate.

20. A compound according to claim 1 which is 2-(2-methoxyethoxy)ethyl 3-(3,4,5-trimethoxybenzoyl)propiolate.

21. A compound according to claim 1 which is 2-(2-methoxyethoxy)ethyl 3-(4-methoxybenzoyl)propiolate.

22. A compound according to claim 1 which is methyl 3-(2,5-dimethoxybenzoyl)propiolate.

23. A compound according to claim 1 which is 3-(2,5-dimethoxybenzoyl)propiolic acid.

24. A compound according to claim 1 which is 2-(2-methoxyethoxy)ethyl 3-[3,4-(methylenedioxy)benzoyl]propiolate.

25. A compound according to claim 1 which is selected from the group consisting of:
3-(2,3,4-trimethoxybenzoyl)propiolic acid;
3-(3,4,5-trimethoxybenzoyl)propiolic acid;
methyl 3-(4-fluorobenzoyl)propiolate;
methyl 3-(3,4,5-trimethoxybenzoyl)propiolate;
N,N-dimethyl-3-(3,4,5-trimethoxybenzoyl)propiolamide;
1-(4-fluorophenyl)-4-hydroxy-2-butyn-1-one;
4-hydroxy-1-(4-methylphenyl)-2-butyn-1-one;
4-(1-ethoxyethoxy)-1-(4-fluorophenyl)-2-butyn-1-one;
1-(4-chlorophenyl)-4-hydroxy-2-butyn-1-one;
4-hydroxy-1-(4-methoxyphenyl)-2-butyn-1-one;
4-hydroxy-1-[3,4-(methylenedioxy)phenyl]-2-butyn-1-one;
4-hydroxy-1-(3,4,5-trimethoxyphenyl)-2-pentyn-1-one;
4-(1-ethoxyethoxy)-1-(2,3,4-trimethoxyphenyl)-2-butyn-1-one;
4-hydroxy-1-(2,3,4-trimethoxyphenyl)-2-butyn-1-one; and
4-hydroxy-1-[4-(methylthio)phenyl]-2-butyn-1-one.

* * * * *

UNITED STATES PATENT AND TRADEMARK OFFICE
CERTIFICATE OF CORRECTION

PATENT NO. : 4,929,741
DATED : May 29, 1990
INVENTOR(S) : Fischli et al.

It is certified that error appears in the above-identified patent and that said Letters Patent is hereby corrected as shown below:

In claim 4, column 36, line 33, insert --alkoxy-- between "lower" and ".";

In claim 5, column 36, line 35, insert --alkoxy-- between "lower" and ".";

In claim 6, column 36, line 37, insert --alkoxy-- between "lower" and ".";

In claim 8, column 36, line 44, insert "alkylamino-- between "lower" and ".";

In claim 13, column 37, line 3, insert --$R^{14}$-between"methyl;" and "is".

Signed and Sealed this

Twenty-fourth Day of September, 1991

Attest:

HARRY F. MANBECK, JR.

Attesting Officer

Commissioner of Patents and Trademarks